(12) United States Patent
Ohtani et al.

(10) Patent No.: US 12,172,951 B2
(45) Date of Patent: Dec. 24, 2024

(54) ANTHRAQUINONE COMPOUND, LIQUID CRYSTAL COMPOSITION CONTAINING SAID COMPOUND, AND DIMMING ELEMENT

(71) Applicant: Nippon Kayaku Kabushiki Kaisha, Tokyo (JP)

(72) Inventors: Kohei Ohtani, Tokyo (JP); Masakazu Shiraishi, Tokyo (JP); Hitomi Muto, Tokyo (JP); Saori Suzuki, Tokyo (JP); Kanae Ogawa, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/283,329

(22) PCT Filed: Apr. 11, 2022

(86) PCT No.: PCT/JP2022/017467
§ 371 (c)(1),
(2) Date: Sep. 21, 2023

(87) PCT Pub. No.: WO2022/220212
PCT Pub. Date: Oct. 20, 2022

(65) Prior Publication Data
US 2024/0140907 A1    May 2, 2024

(30) Foreign Application Priority Data
Apr. 14, 2021   (JP) .................. 2021-068179

(51) Int. Cl.
*G02F 1/1333*   (2006.01)
*C07C 323/38*   (2006.01)
*C09B 1/58*   (2006.01)
*C09K 19/10*   (2006.01)

(52) U.S. Cl.
CPC .............. *C07C 323/38* (2013.01); *C09B 1/58* (2013.01); *C09K 19/10* (2013.01)

(58) Field of Classification Search
CPC ........ C09K 19/60; C09K 19/602; C09B 1/58; G02F 1/1333; G02F 1/13439; G02F 1/13725
See application file for complete search history.

(56) References Cited

U.S. PATENT DOCUMENTS

| | | | |
|---|---|---|---|
| 11,905,417 B2 * | 2/2024 | Ohtani | C09B 1/585 |
| 2018/0307077 A1 | 10/2018 | Miura et al. | |
| 2024/0140907 A1 * | 5/2024 | Ohtani | C07C 323/38 |
| 2024/0141234 A1 * | 5/2024 | Muto | C09K 19/542 |
| 2024/0150657 A1 * | 5/2024 | Ogawa | C09K 19/603 |

FOREIGN PATENT DOCUMENTS

| | | |
|---|---|---|
| EP | 0059036 A1 | 9/1982 |
| EP | 0244488 A1 | 11/1987 |
| JP | 62-64865 A | 3/1987 |
| JP | 62-101657 A | 5/1987 |
| JP | 63-72759 A | 4/1988 |
| JP | 63-72760 A | 4/1988 |
| JP | 63-501512 A | 6/1988 |
| JP | 63-278969 A | 11/1988 |
| JP | 3-47392 A | 2/1991 |
| JP | 2011-190314 A | 9/2011 |
| JP | 2018-205746 A | 12/2018 |
| WO | 87/01822 A1 | 3/1987 |

* cited by examiner

*Primary Examiner* — Geraldina Visconti
(74) *Attorney, Agent, or Firm* — NIELDS, LEMACK & FRAME, LLC

(57) ABSTRACT

The present invention is an anthraquinone compound represented by formula (1) (in the formula. $R_1$ represents a hydrogen atom, a C1-C12 linear or branched alkyl group, or a C1-C12 linear or branched alkoxy group, and $R_2$ represents a substituent represented by: formula (a) (in formula (a), $R_3$ represents a hydrogen atom, a C1-C8 linear or branched alkyl group, a C1-C8 linear or branched alkoxy group, or a substituent represented by —$CH_2OR_4$, where $R_4$ represents a C1-C8 linear or branched alkyl group); or formula (b) (in formula (b). $R_5$ represents a hydrogen atom, a C1-C8 linear or branched alkyl group, or a substituent represented by —$CH_2OR_6$, where $R_6$ represents a C1-C8 linear or branched alkyl group)).

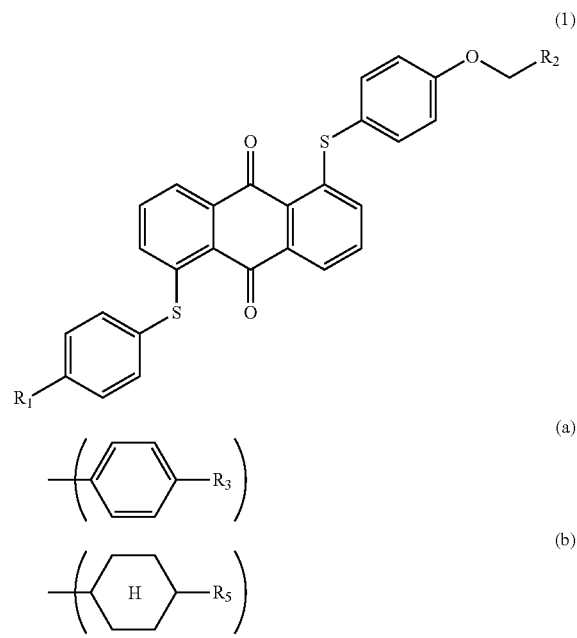

20 Claims, No Drawings

ANTHRAQUINONE COMPOUND, LIQUID CRYSTAL COMPOSITION CONTAINING SAID COMPOUND, AND DIMMING ELEMENT

TECHNICAL FIELD

The present invention relates to a novel anthraquinone compound, and a liquid crystal composition and a light control element that contain the compound.

BACKGROUND ART

For windows, doors, partitions, and the like in vehicles such as trains and automobiles and buildings such as business and hospital buildings, various devices have been proposed that relate to light control films for control of transmission of external light for the purpose of, for example, protecting privacy (see PATENT LITERATUREs 1 and 2). One of such light control films utilizes a liquid crystal. Usually, a liquid crystal light control film can block the field of view by controlling transmission and scattering of light according to presence or absence of an applied voltage, but cannot block light itself, and therefore the light scattering tends to increase glare. Therefore, for the purpose of reduction in glare, improvement in contrast, and the like, attempts have been made to use a dye as a material of a light control panel (see PATENT LITERATUREs 3 and 4). For example, such a light control panel to be used in a window glass of an automobile is required to be free from fogging to provide good visibility when transparent, and in addition, required to be deeply colored when blocking light, required to have light resistance such that the transmittance does not decrease even under irradiation with light for a long time at high temperatures due to the influence of long-term exposure in outdoor use, and required to have heat resistance after energization such that the transmittance does not decrease even when a voltage is applied for a long time at high temperatures.

A dye used in a liquid crystal light control film is generally a dichroic dye. As a light control element using a liquid crystal composition containing a dichroic dye, GH (guest-host) elements have been known, and various dichroic dyes have been proposed (see PATENT LITERATUREs 5, 6, and 7).

Such dichroic dyes are required to have not only contrast but also light resistance, heat resistance after energization, and the like when used as a display element. Efforts have been made to improve these characteristics, but a dichroic dye has not been found that can satisfy contrast, light resistance, and heat resistance after energization. For example, PATENT LITERATUREs 5, 6 and 7 disclose dichroic dyes suitable for use for light control, but the dyes in PATENT LITERATUREs 5, 6 and 7 are insufficient in contrast, light resistance, and heat resistance after energization.

CITATION LIST

Patent Literature

PATENT LITERATURE 1: JP-A-63-501512
PATENT LITERATURE 2: JP-A-03-47392
PATENT LITERATURE 3: JP-A-2018-205746
PATENT LITERATURE 4: JP-A-2011-190314
PATENT LITERATURE 5: JP-A-63-72760
PATENT LITERATURE 6: JP-A-62-101657
PATENT LITERATURE 7: EP 59036 A1

SUMMARY OF INVENTION

Technical Problem

A first object of the present invention is to provide a novel anthraquinone compound.

Another object of the present invention is to provide a dichroic dye that is the novel anthraquinone compound, a liquid crystal composition containing the anthraquinone compound, and a light control element containing the composition and being excellent in contrast, light resistance, and heat resistance after energization.

Solution to Problem

The present inventors have succeeded in obtaining a novel anthraquinone compound having a specific structure.

Furthermore, the present inventors have found that a light control element excellent in contrast, light resistance, and heat resistance after energization can be obtained by using a liquid crystal composition containing a dichroic dye that is such a novel anthraquinone compound having a specific structure described above.

That is, aspects included in the present invention are as follows.

[1]. An anthraquinone compound represented by Formula) described below:

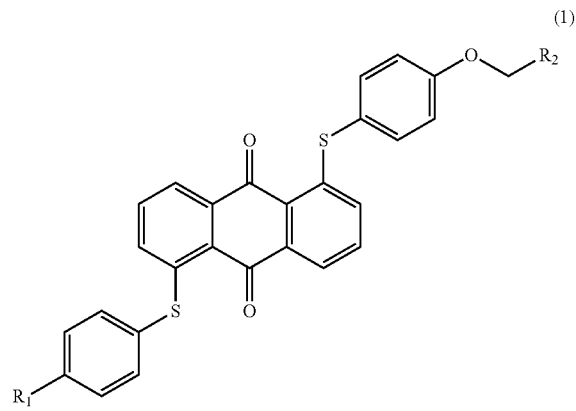

(1)

wherein $R_1$ represents a hydrogen atom, a C1-C12 linear or branched alkyl group, or a C1-C12 linear or branched alkoxy group, and $R_2$ represents a substituent represented by Formula (a) described below:

(a)

wherein $R_3$ represents a hydrogen atom, a C1-C8 linear or branched alkyl group, a C1-C8 linear or branched alkoxy group, or a substituent represented by $-CH_2OR_4$ wherein $R_4$, represents a C1-C8 linear or branched alkyl group or $R_2$ represents a substituent represented by Formula (b) described below:

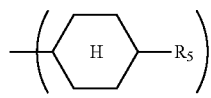

wherein $R_5$ represents a hydrogen atom, a C1-C8 linear or branched alkyl group, or a substituent represented by —$CH_2OR_6$ wherein $R_6$ represents a C1-C8 linear or branched alkyl group.

[2] The anthraquinone compound according to the item [1], wherein $R_2$ in Formula (1) represents a substituent represented by Formula (a), and $R_3$ in Formula (a) represents a hydrogen atom, a C1-C8 linear or branched alkyl group, or a C1-C8 linear or branched alkoxy group.

[3]. The anthraquinone compound according to the item [2], wherein $R_3$ in Formula (a) represents a hydrogen atom or a C1-C8 linear or branched alkyl group.

[4]. The anthraquinone compound according to the item [1], wherein $R_2$ in Formula (1) represents a substituent represented by Formula (b), and $R_5$ in Formula (b) represents a, hydrogen atom or a C1-C8 linear or branched alkyl group.

[5]. The anthraquinone compound according to any one of the items [1] to [4], wherein $R_1$ in Formula (1) represents a C1-C8 linear or branched alkoxy group.

[6]. The anthraquinone compound according to the item [5], wherein $R_1$ in Formula (represents a C4-C8 linear alkoxy group.

[7]. The anthraquinone compound according to any one of the items [1] to [4], wherein $R_1$ in Formula (1) represents a hydrogen atom or a C1-C8 linear or branched alkyl group.

[8]. The anthraquinone compound according to the item [7], wherein $R_1$ in Formula (1) represents a C4-C8 linear alkyl group.

[9]. A liquid crystal composition comprising the anthraquinone compound according to any one of the items [1] to [8] and a liquid crystal material.

[10]. The liquid crystal composition according to the item [9], further comprising a photocurable compound and a photopolymerization initiator.

[11]. The liquid crystal composition according to the item [9] or [10], further comprising at least one dye compound other than the anthraquinone compound according to the item [1].

[12]. A photocured product of the liquid crystal composition according to the item or [11].

[13]. A light control element comprising: a pair of substrates disposed to face to each other; and the liquid crystal composition according to any one of the items [9] to [11] or the photocured product according to the item [12] sandwiched between the pair of substrates, wherein at least one substrate in the pair of substrates is a transparent substrate having a transparent electrode.

[14]. The light control element according to the item [13], wherein both substrates in the pair of substrates are a transparent substrate having a transparent electrode.

Advantageous Effects of Invention

According to the present invention, a novel anthraquinone compound is provided.

Furthermore, a light control element excellent in contrast, light resistance, and heat resistance after energization can be obtained by using a liquid crystal composition containing the anthraquinone compound of the present invention.

DESCRIPTION OF EMBODIMENTS

Hereinafter, the present invention will be described in detail.

The anthraquinone compound of the present invention is represented by Formula (1) described below.

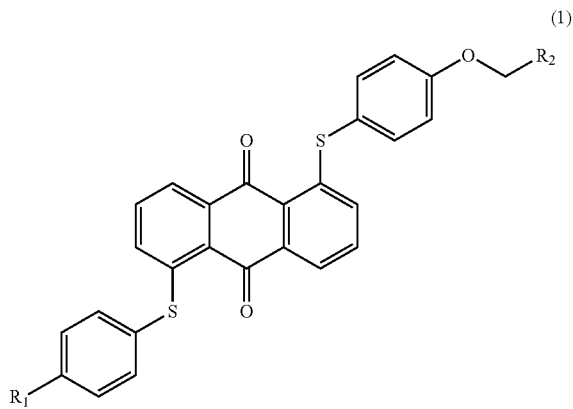

In Formula (1), $R_1$ represents a hydrogen atom, a C1-C12 linear or branched alkyl group, or a C1-C12 linear or branched alkoxy group.

The C1-C12 alkyl group represented by $R_1$ in Formula (1) may be linear or branched. Specific examples of the alkyl group include a methyl group, an ethyl group, an n-propyl group, an iso-propyl group, an n-butyl group, an iso-butyl group, a sec-butyl group, a t-butyl group, an n-pentyl group, an iso-pentyl group, a neo-pentyl group, a t-pentyl group, a hexyl group, a heptyl group, an octyl group, a nonyl group, a decyl group, an undecyl group, a dodecyl group, a 2-ethylhexyl group, a 2-propythexyl group, a 2-butylhexyl group, a 2-pentylhexyl group, and a 2-pentylheptyl group. A C1-C8 linear or branched alkyl group is preferable, a C4-C8 linear or branched alkyl group is more preferable, and a C4-C8 linear alkyl group is still more preferable.

The A C1-C12 alkoxy group represented by $R_1$ in Formula (1) may be linear or branched. Specific examples of the alkoxy group include a methoxy group, an ethoxy group, an n-propoxy group, an iso-propoxy group, an n-butoxy group, an iso-butoxy group, a sec-butoxy group, a t-butoxy group, an n-pentyloxy group, an iso-pentyloxy group, a neo-pentyloxy group, a t-pentyloxy group, a hexyloxy group, a heplyloxy group, an octyloxy group, a nonyloxy group, a decyloxy group, an undecyloxy group, a dodecyloxy group, a 2-ethythexyloxy group, a 2-propylhexyloxy group, a 2-butylhexyloxy group, a 2-pentylhexyloxy group, and a 2-pentylheptyloxy group. A C1-C8 linear or branched alkoxy group is preferable, a C4-C8 linear or branched alkoxy group is more preferable, and a C4-C8 linear alkoxy group is still more preferable.

$R_1$ in Formula (1) is preferably a C1-C8 linear or branched alkyl group or a C1-C8 linear or branched alkoxy group, and more preferably a C4-C8 linear alkyl group or a C4-C8 linear alkoxy group.

In Formula (1), $R_2$ represents a substituent represented by Formula (a) or (b) described below.

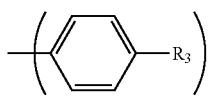

(a)

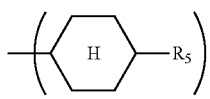

(b)

In Formula (a), $R_3$ represents a hydrogen atom, a C1-C8 linear or branched alkyl group, a C1-C8 linear or branched alkoxy group, or a substituent represented by —$CH_2OR_4$, and $R_4$ represents a C1-C8 linear or branched alkyl group.

The C1-C8 alkyl group represented by $R_3$ in Formula (a) may be linear or branched. Specific examples of the alkyl group include a methyl group, an ethyl group, an n-propyl group, an iso-propyl group, an n-butyl group, an iso-butyl group, a sec-butyl group, a t-butyl group, an n-pentyl group, an iso-pentyl group, a neo-pentyl group, a t-pentyl group, a hexyl group, a heptyl group, an octyl group, and a 2-ethythexyl group. A C1-C4 linear or branched alkyl group is preferable, and a C3 or C4 branched alkyl group is more preferable.

The C1-C8 alkoxy group represented by $R_3$ in Formula (a) may be linear or branched.

Specific examples of the alkoxy group include a methoxy group, an ethoxy group, an n-propoxy group, an iso-propoxy group, an n-butoxy group, an iso-butoxy group, a sec-butoxy group, a t-butoxy group, an n-pentyloxy group, an iso-pentyloxy group, a neo-pentyloxy group, a t-pentyloxy group, a hexyloxy group, a heptyloxy group, an octyloxy group, and a 2-ethylhexyloxy group. A C1-C4 linear or branched alkoxy group is preferable, and a C3 or C4 branched alkoxy group is more preferable.

$R_3$ in Formula (a) is preferably a hydrogen atom, a C1-C8 linear or branched alkyl group, or a C1-C8 linear or branched alkoxy group, and more preferably a hydrogen atom or a C1-C8 linear or branched alkyl group.

The C1-C8 alkyl group represented by $R_4$ in the substituent —$CH_2OR_4$ represented by $R_3$ in Formula (a) may be linear or branched. Specific examples of the alkyl group include a methyl group, an ethyl group, an n-propyl group, an iso-propyl group, an n-butyl group, an iso-butyl group, a sec-butyl group, a t-butyl group, an n-pentyl group, an iso-pentyl group, a neo-pentyl group, a t-pentyl group, a hexyl group, a heptyl group, an octyl group, and a 2-ethylhexyl group. A C2-C6 linear or branched alkyl group is preferable, and a C2-C6 linear alkyl group is more preferable.

In Formula (b), $R_5$ represents a hydrogen atom, a C1-C8 linear or branched alkyl group, or a structure represented by —$CH_2OR_6$, and $R_6$ represents a C1-C8 linear or branched alkyl group.

The C1-C8 alkyl group represented by $R_5$ in Formula (b) may be linear or branched. Specific examples of the alkyl group include a methyl group, an ethyl group, an n-propyl group, an iso-propyl group, an n-butyl group, an iso-butyl group, a sec-butyl group, a t-butyl group, an n-pentyl group, an iso-pentyl group, a neo-pentyl group, a t-pentyl group, a hexyl group, a heptyl group, an octyl group, and a 2-ethylhexyl group. A C1-C4 linear or branched alkyl group is preferable, and a C3-C4 branched alkyl group is more preferable.

$R_5$ Formula (b) is preferably a hydrogen atom or a C1-C8 linear or branched alkyl group.

The C1-C8 alkyl group represented by $R_6$ in the substituent —$CH_2OR_6$ represented by $R_5$ in Formula (b) may be linear or branched. Specific examples of the alkyl group include a methyl group, an ethyl group, an n-propyl group, an iso-propyl group, an n-butyl group, an iso-butyl group, a sec-butyl group, a t-butyl group, an n-pentyl group, an iso-pentyl group, a neo-pentyl group, a t-pentyl group, a hexyl group, a heptyl group, an octyl group, and a 2-ethylhexyl group. A C2-C6 linear or branched alkyl group is more preferable, and a C2-C6 linear alkyl group is still more preferable.

$R_2$ in Formula (1) is preferably a substituent represented by Formula (a).

Preferred specific examples of the compound represented by Formula (1) include the following compounds, but the present invention is not limited thereto.

No.1

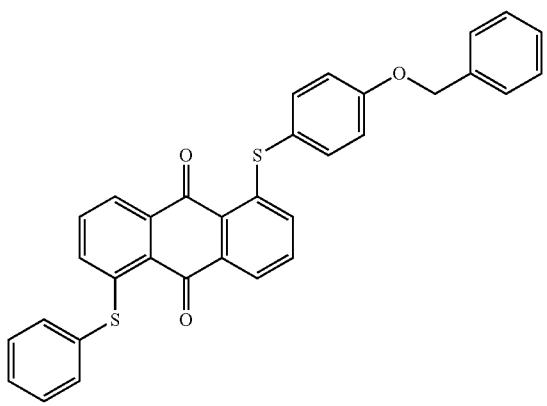

No.2

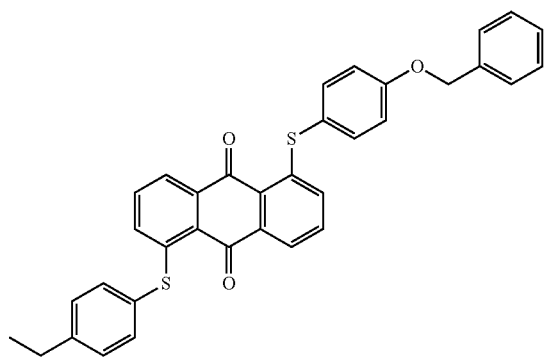

-continued
No.3
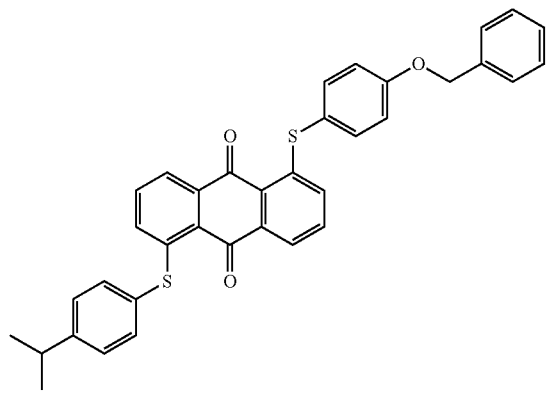
No.4
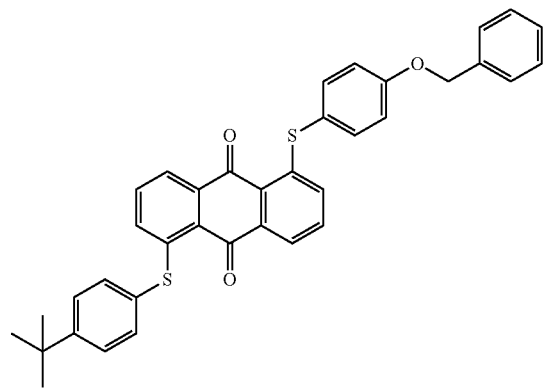
No.5
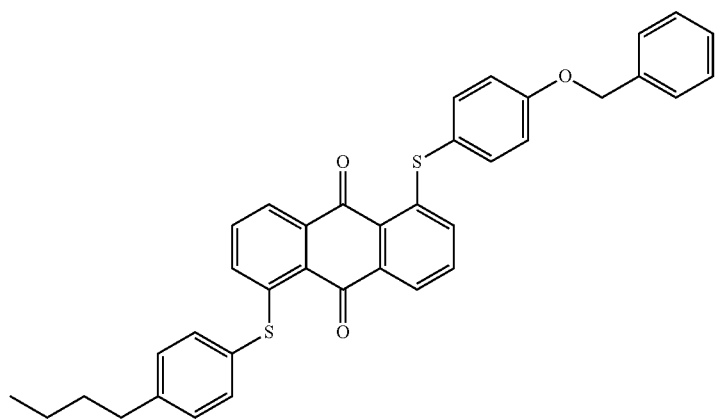
No.6
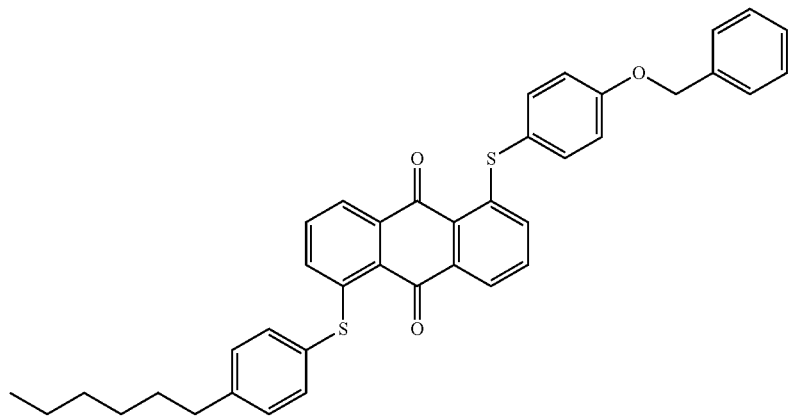

-continued
No.7
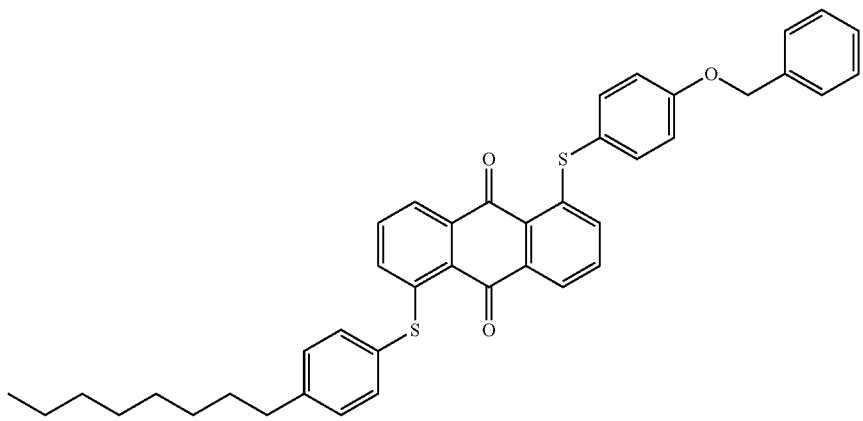
No.8
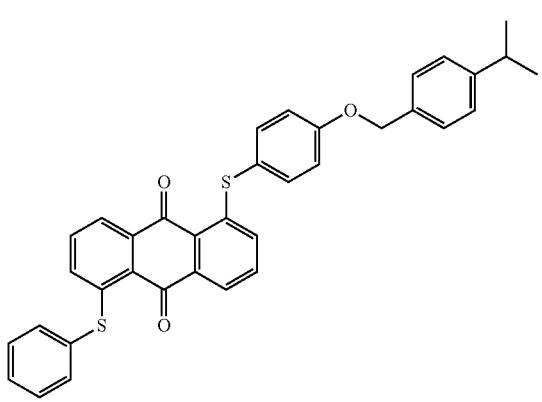
No.9
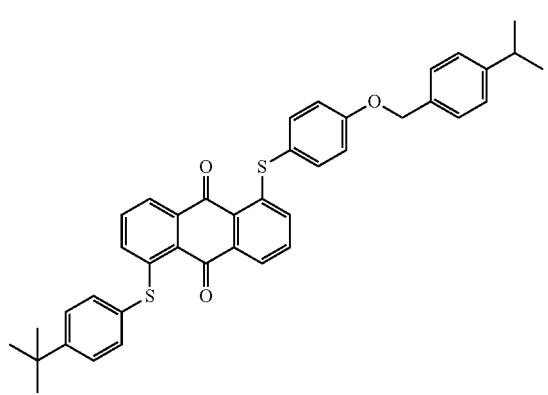
No.10
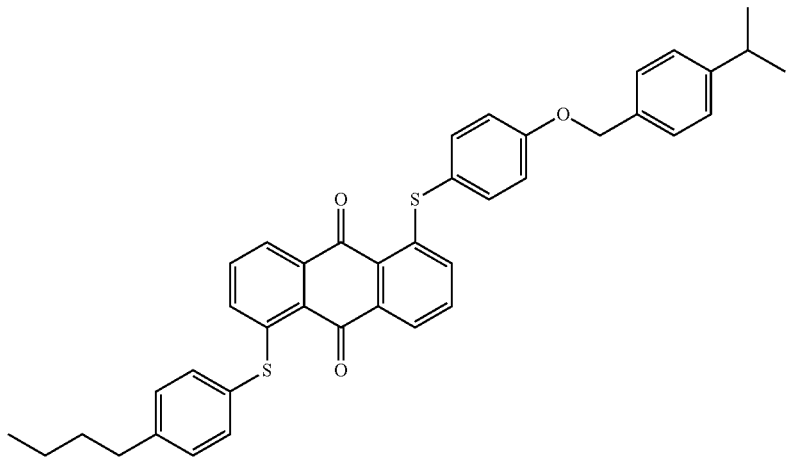

No.11
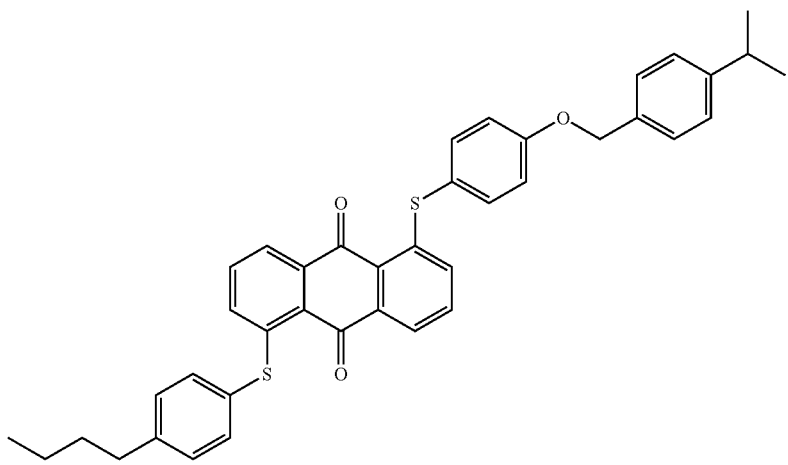
No.12
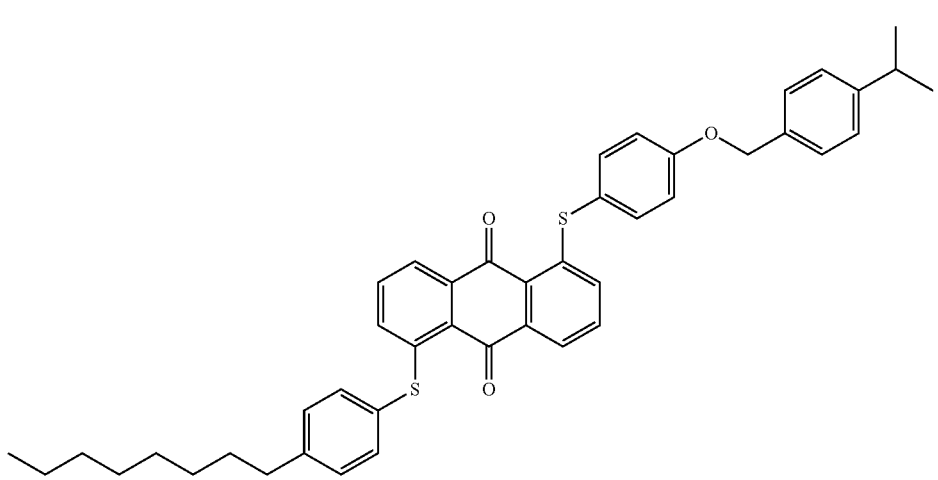
No.13
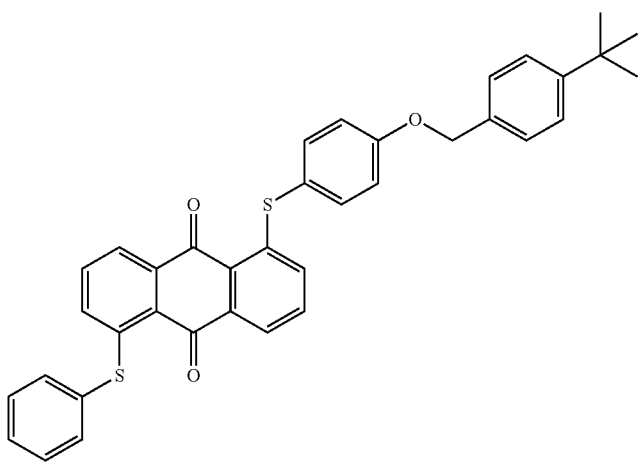

No.14
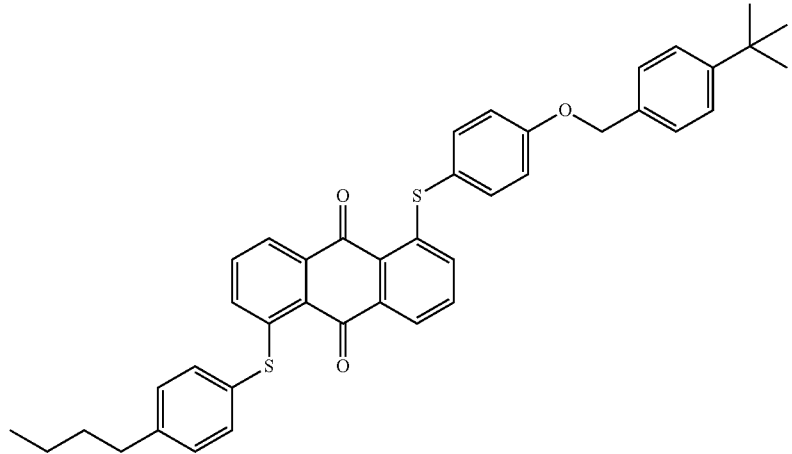
No.15
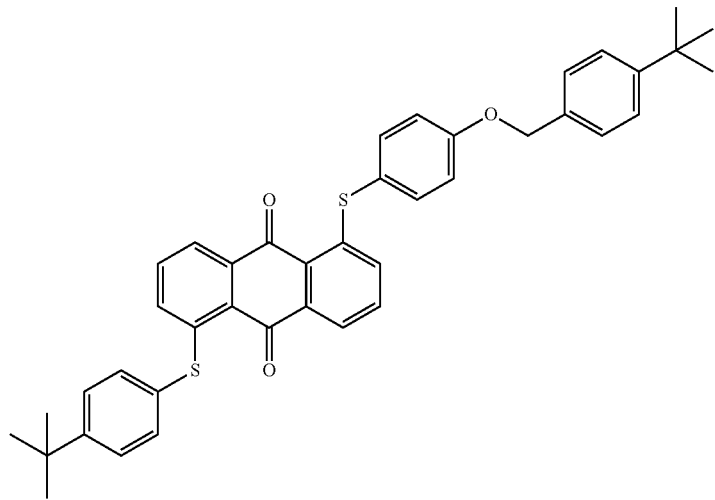
No.16
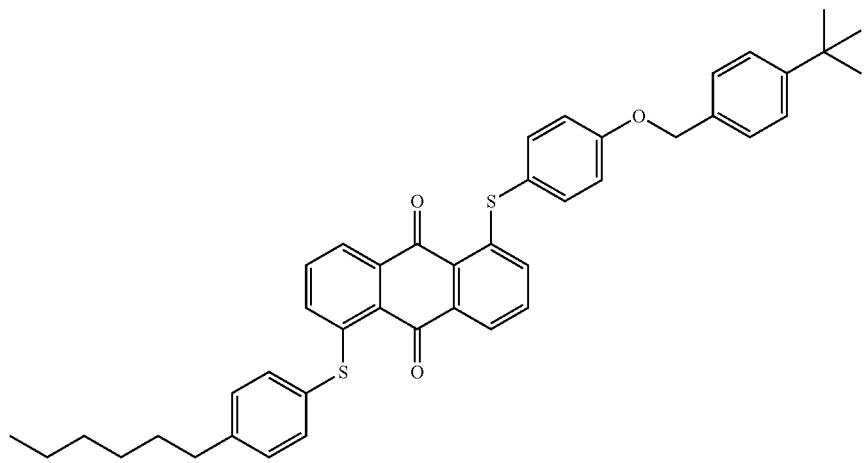

-continued
No.17
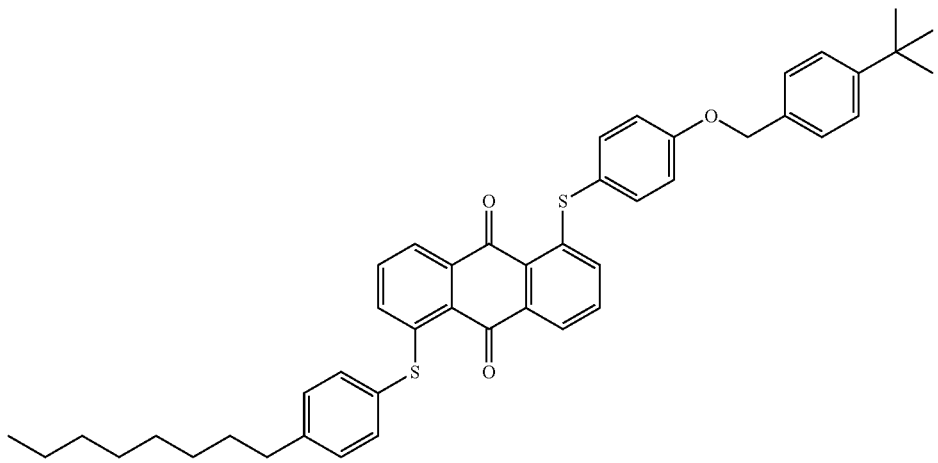
No.18
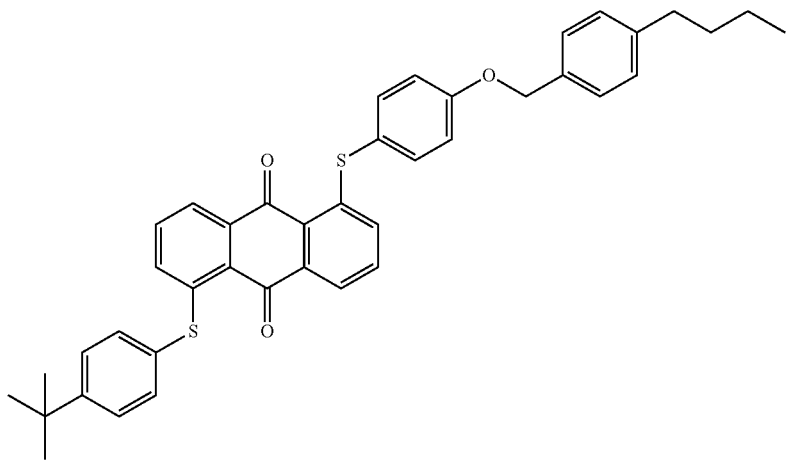
No.19
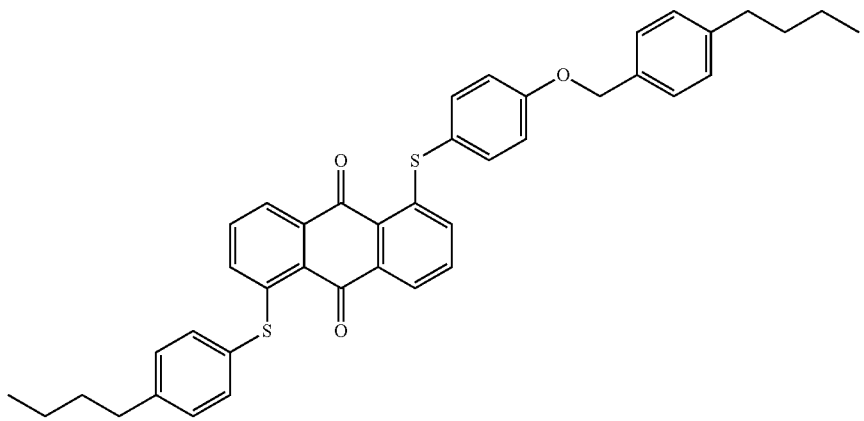

-continued
No.20
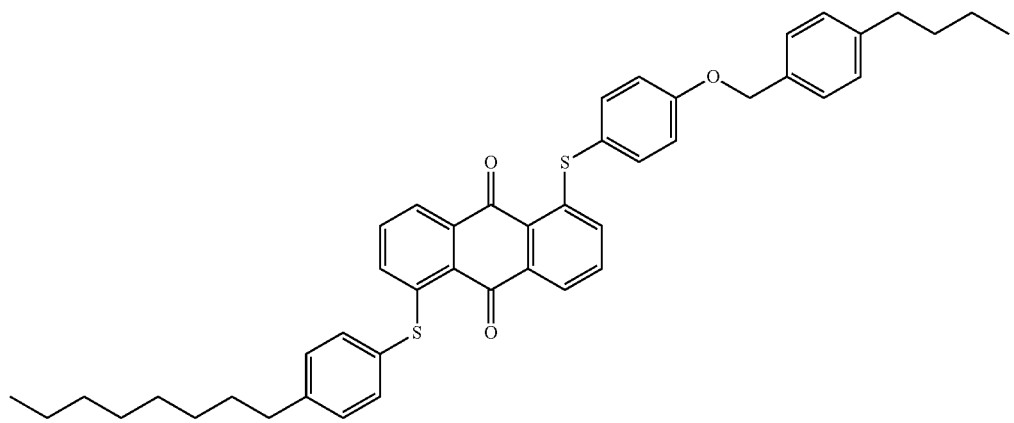
No.21
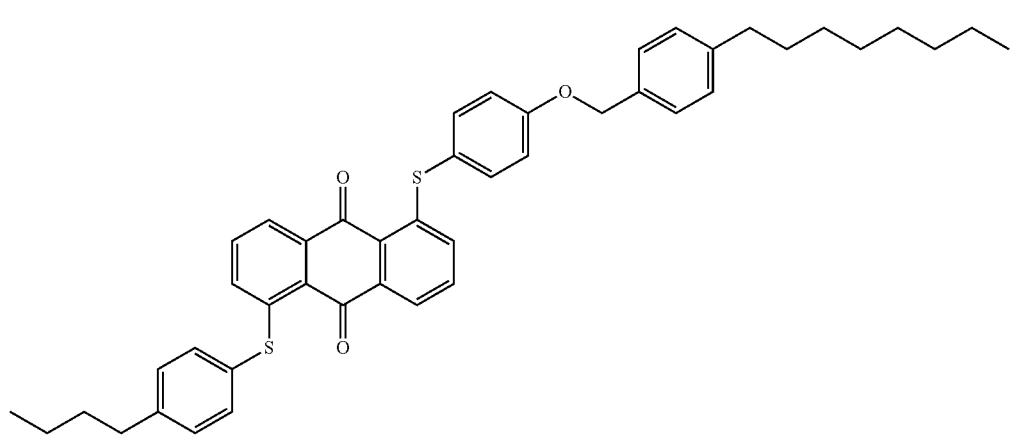
No.22
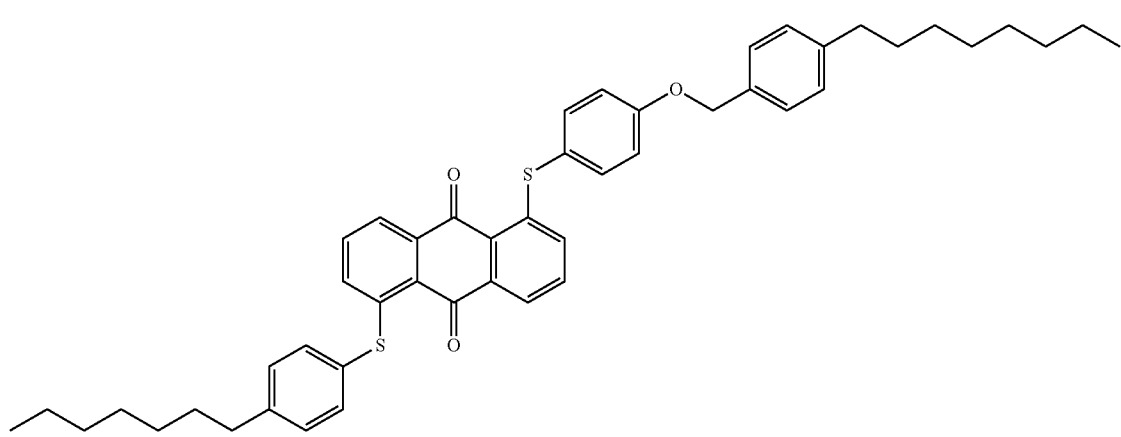

-continued
No.23
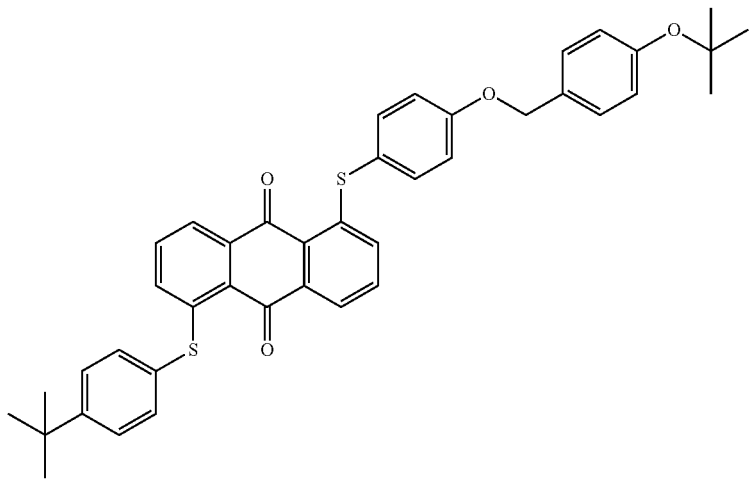
No.24
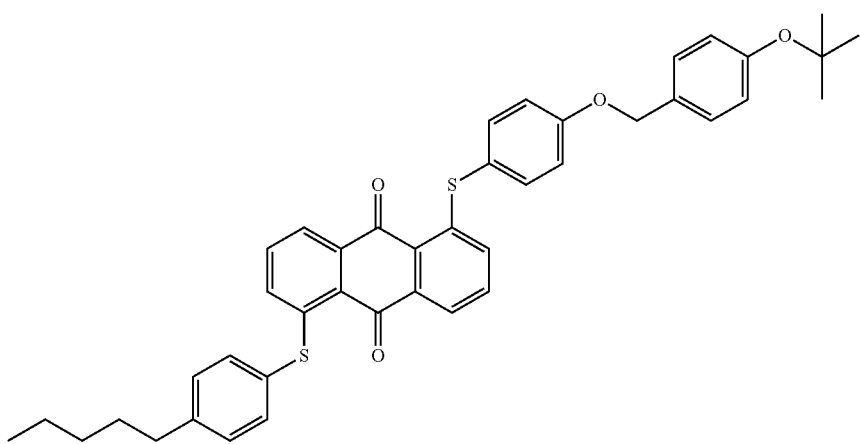
No.25
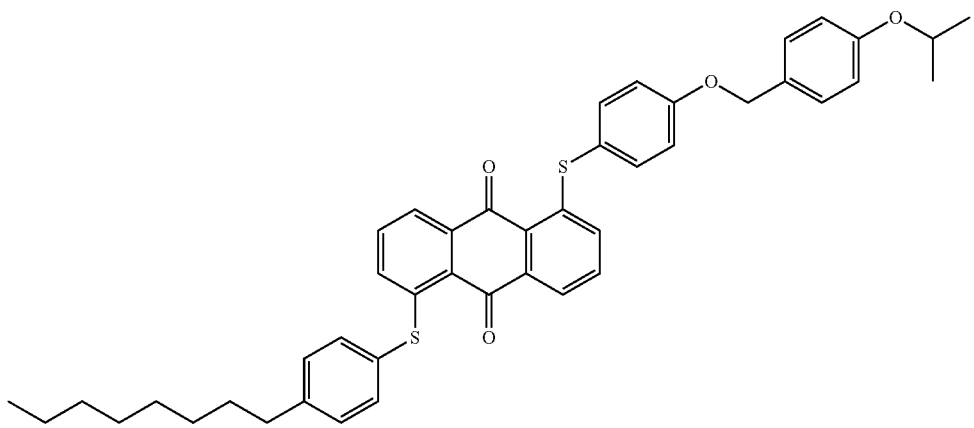

-continued
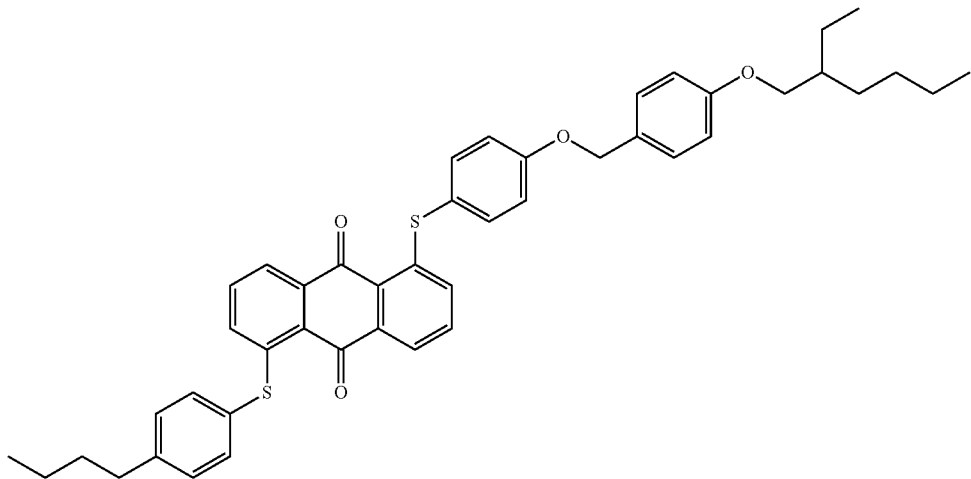
No.26
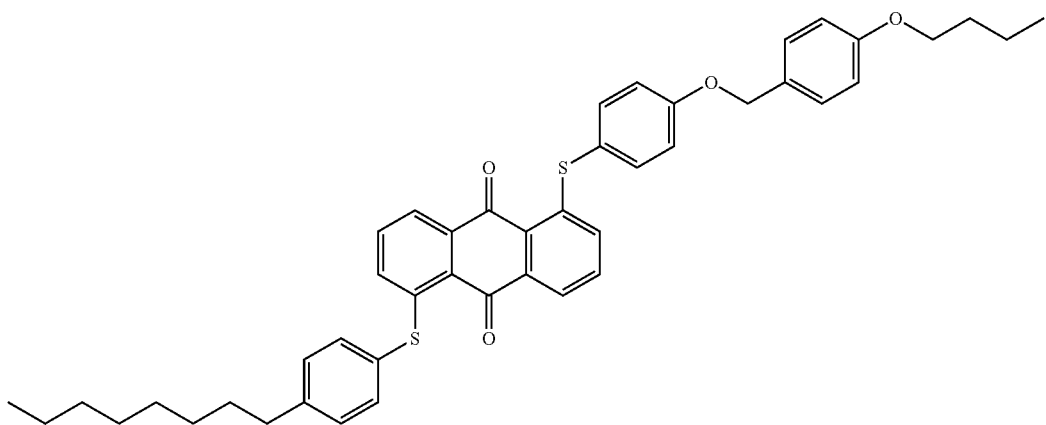
No.27
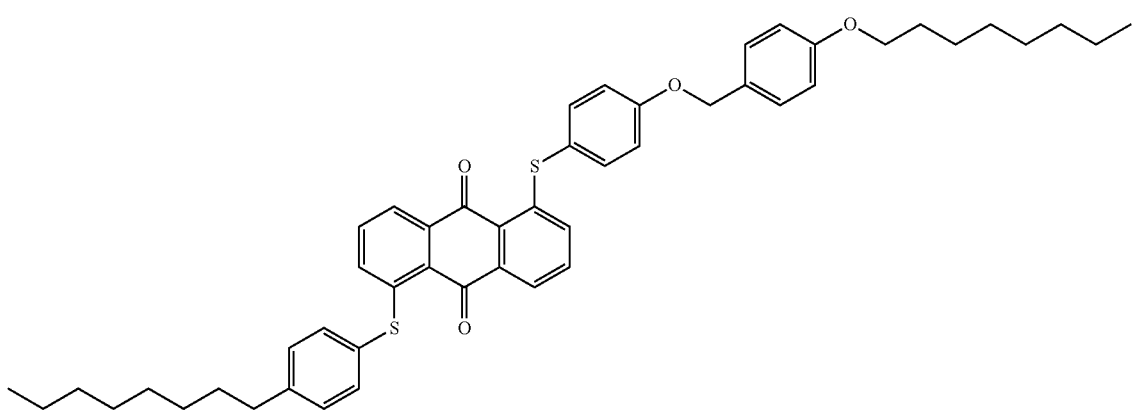
No.28

No.29
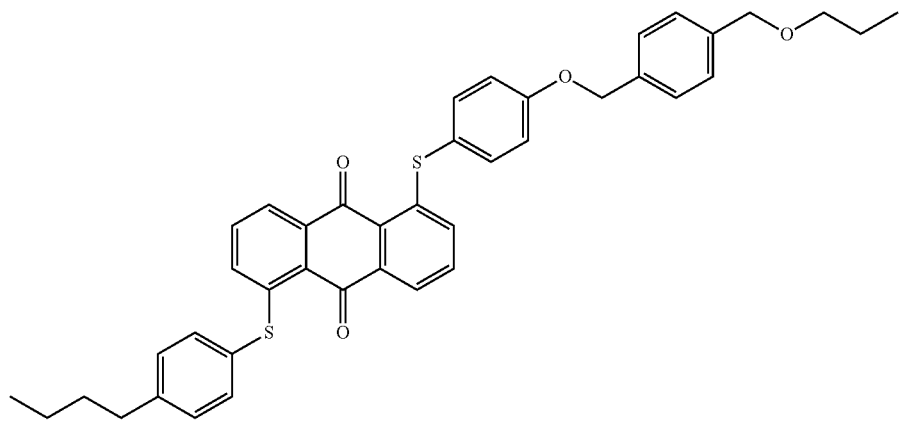
No.30
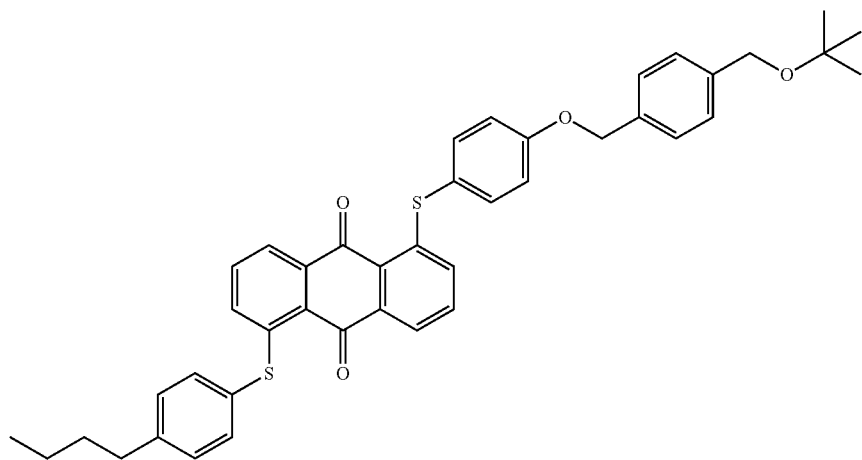
No.31
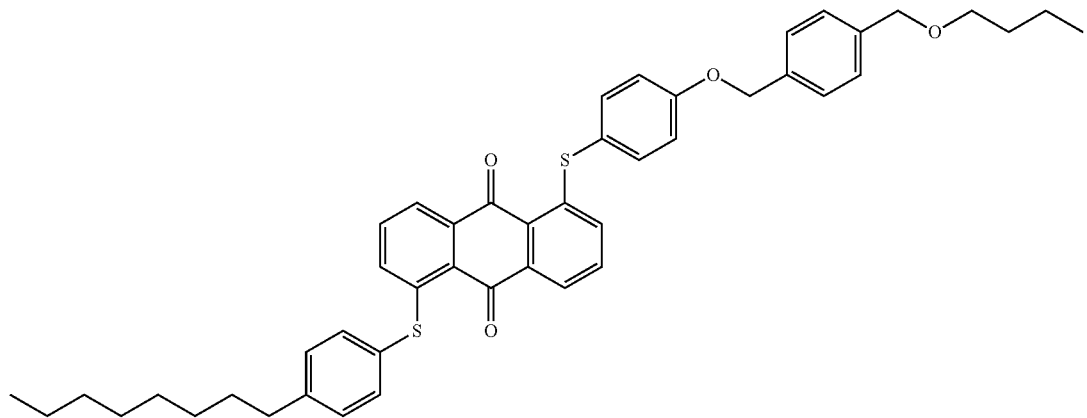

-continued
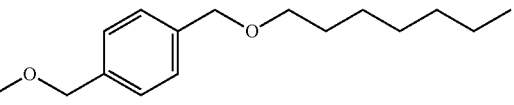
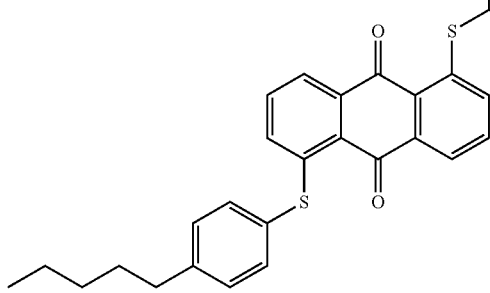
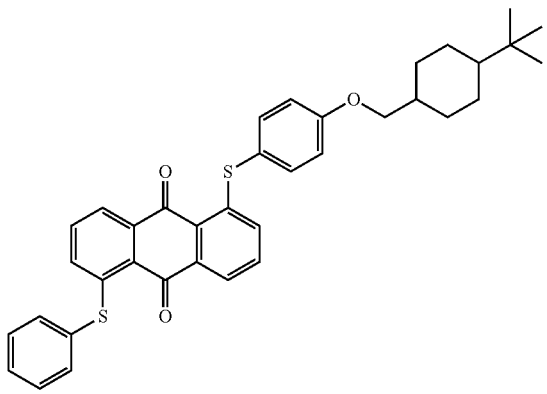
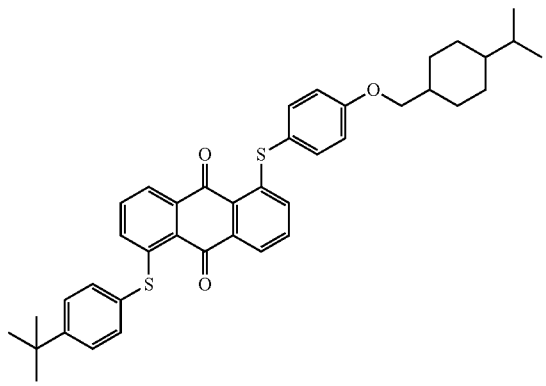
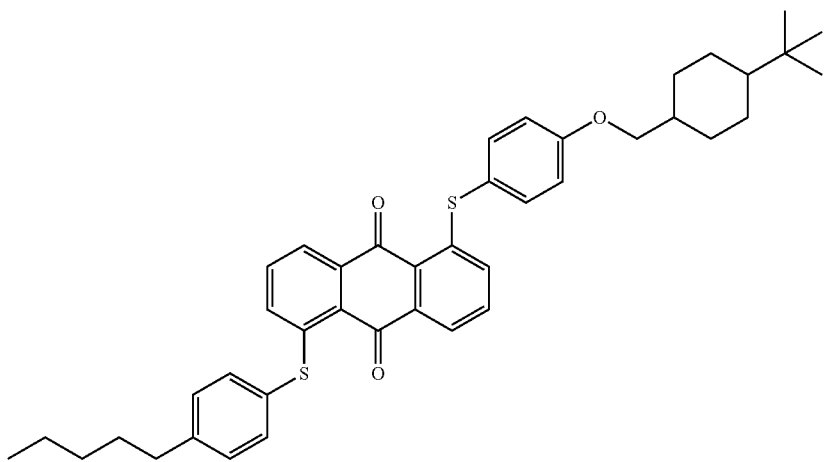

No.36
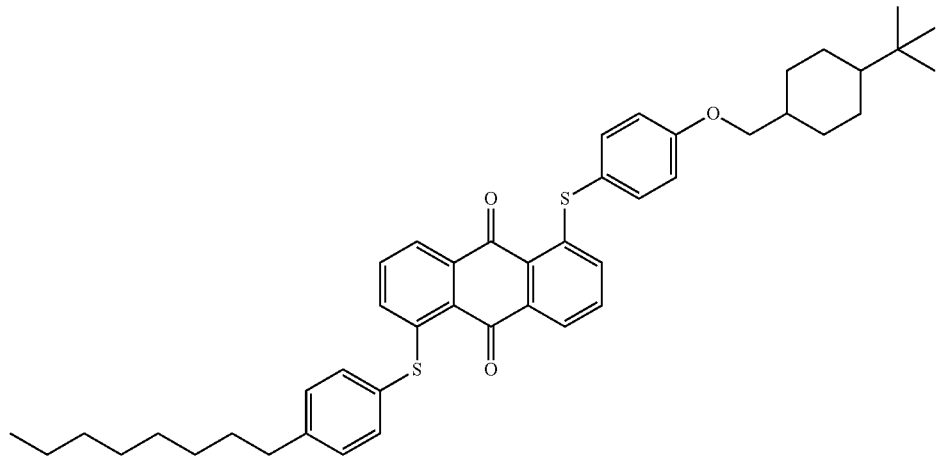
No.37
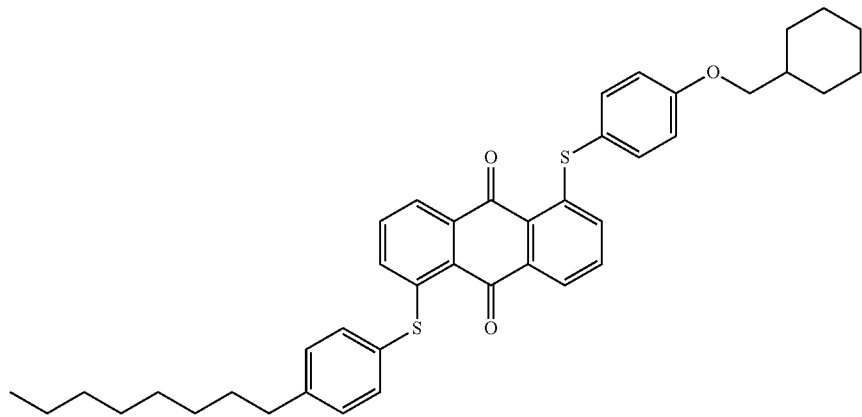
No.38
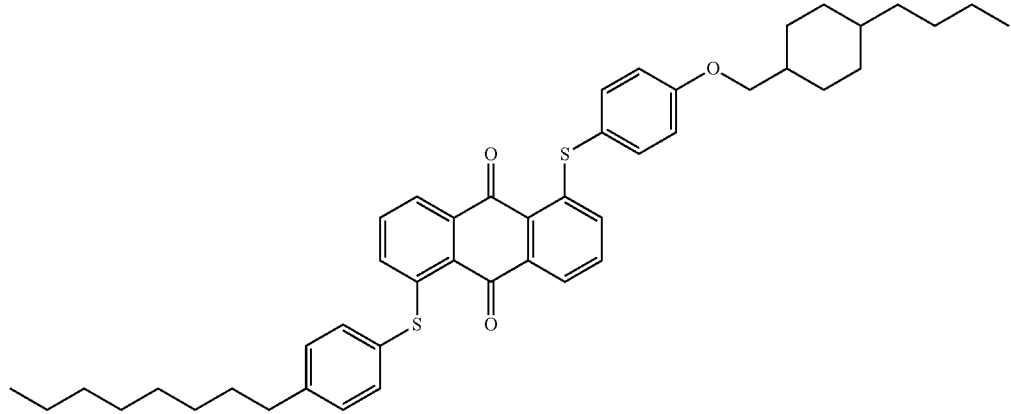

-continued
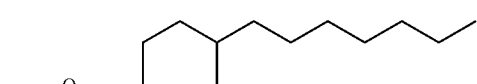
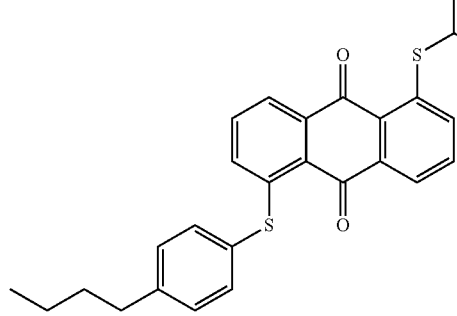
No.39
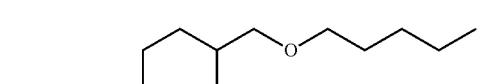
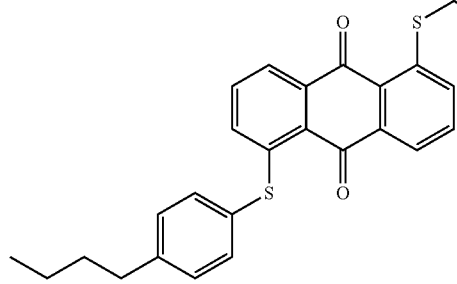
No.40
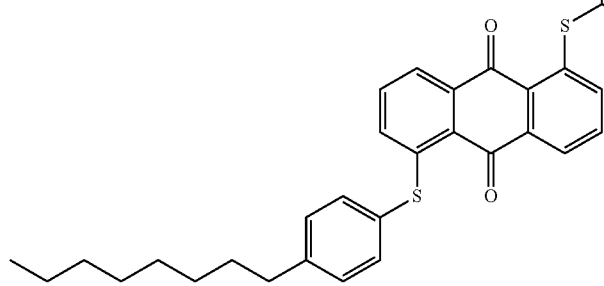
No.41

-continued
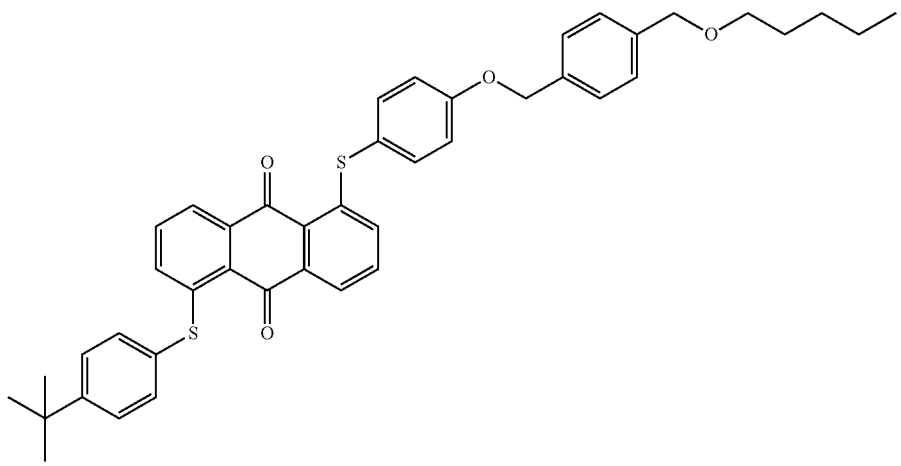
No.42
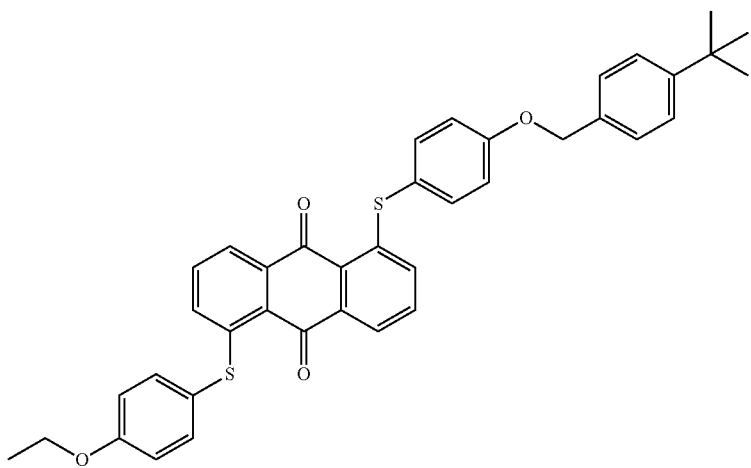
No.43
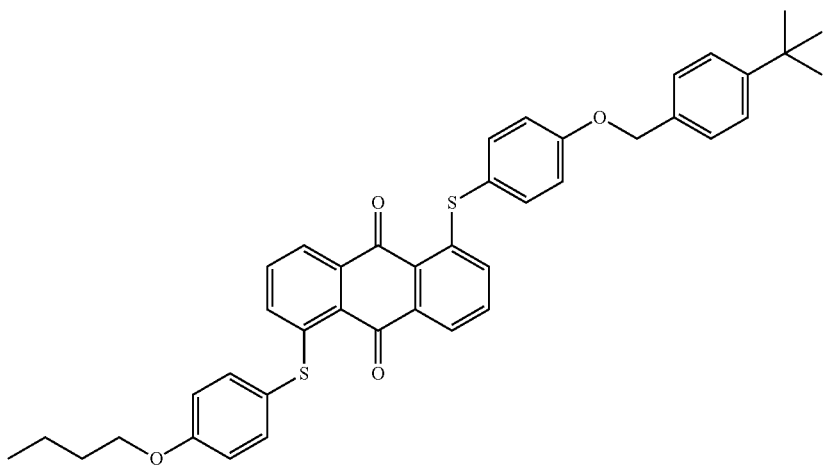
No.44

-continued
No.45
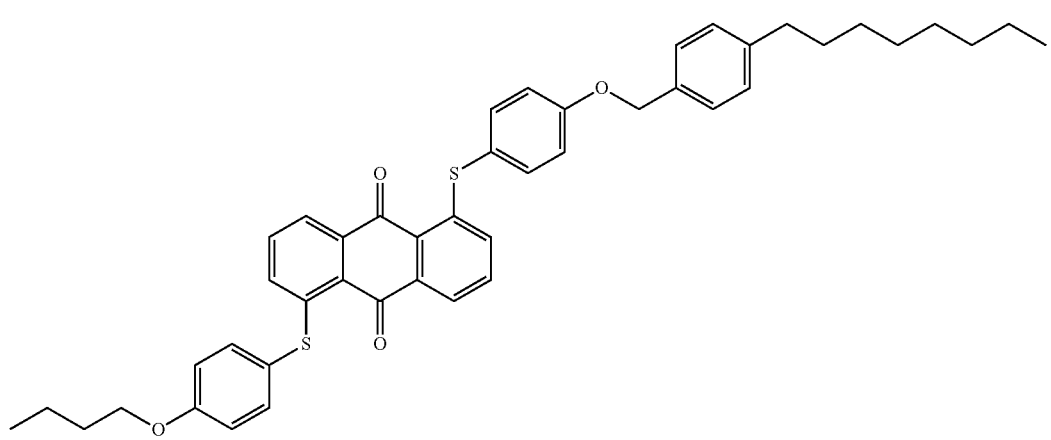
No.46
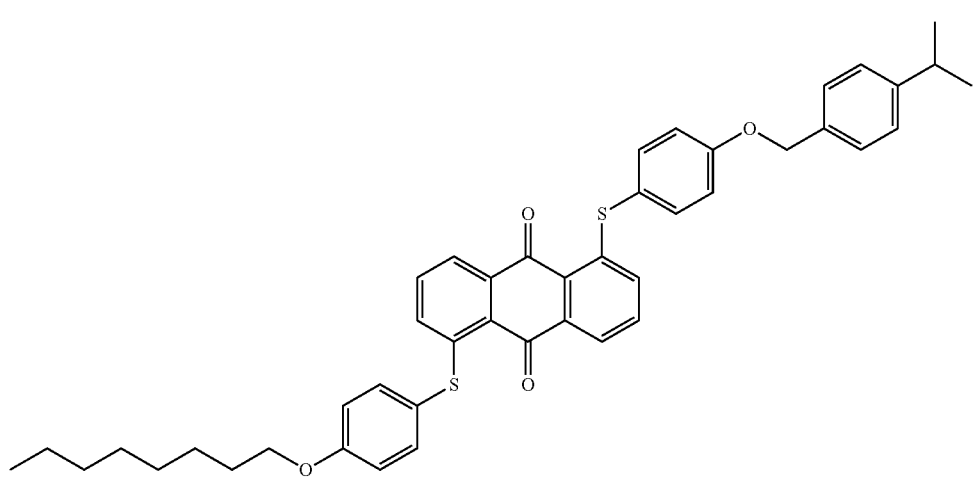
No.47
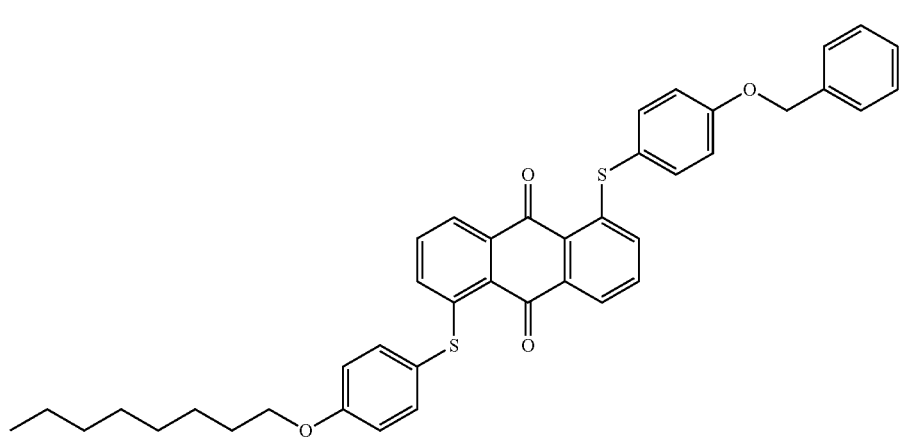

-continued
No.48
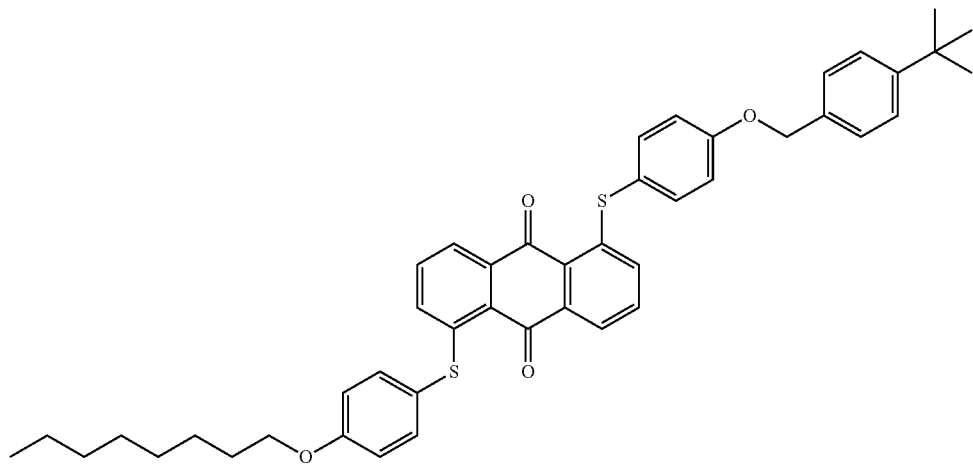
No.49
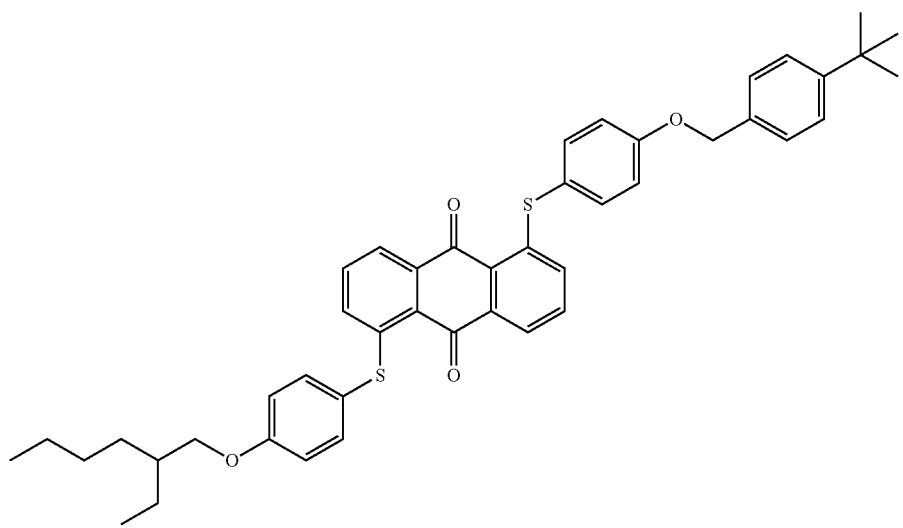
No.50
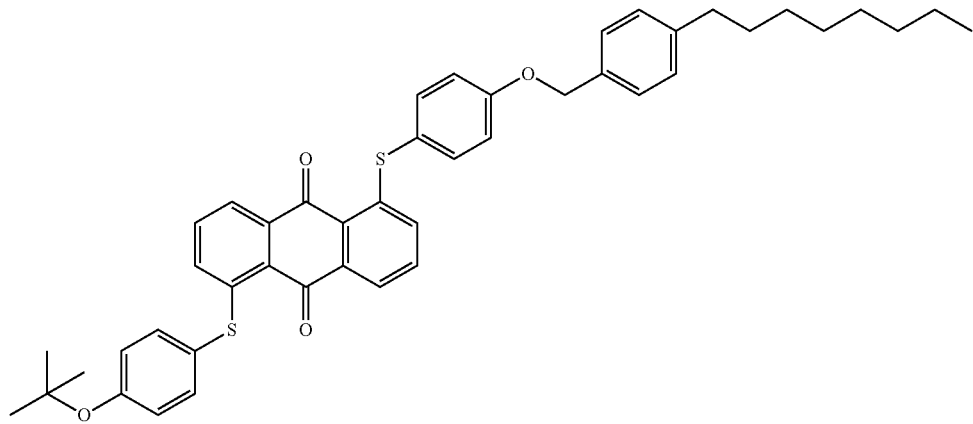

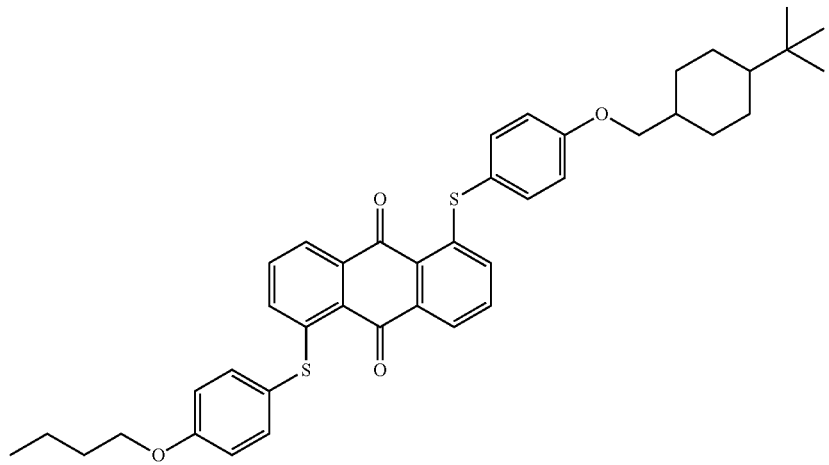
No.51
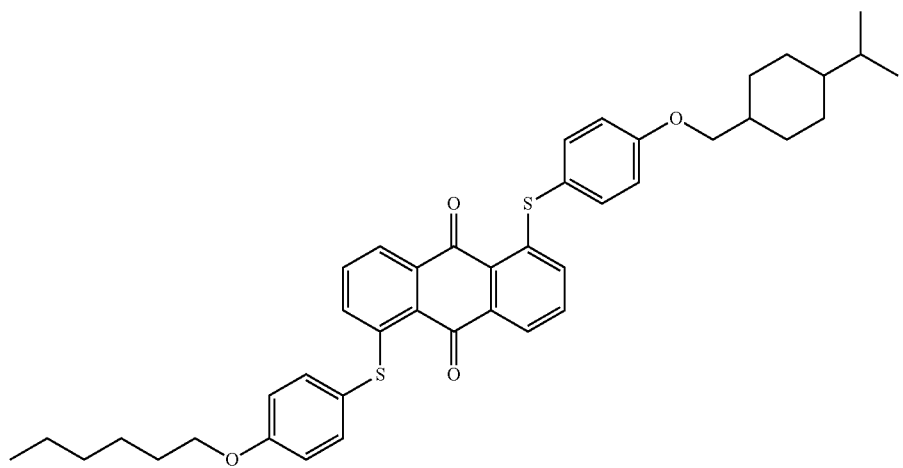
No.52
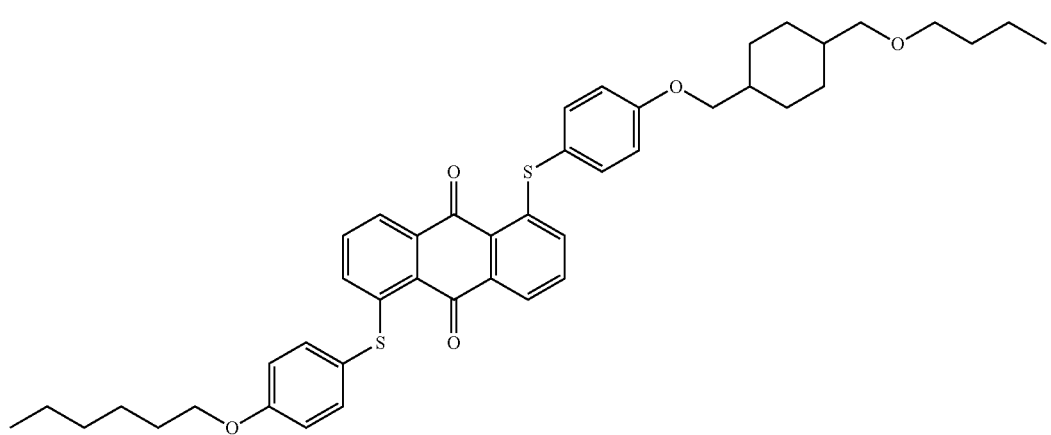
No.53

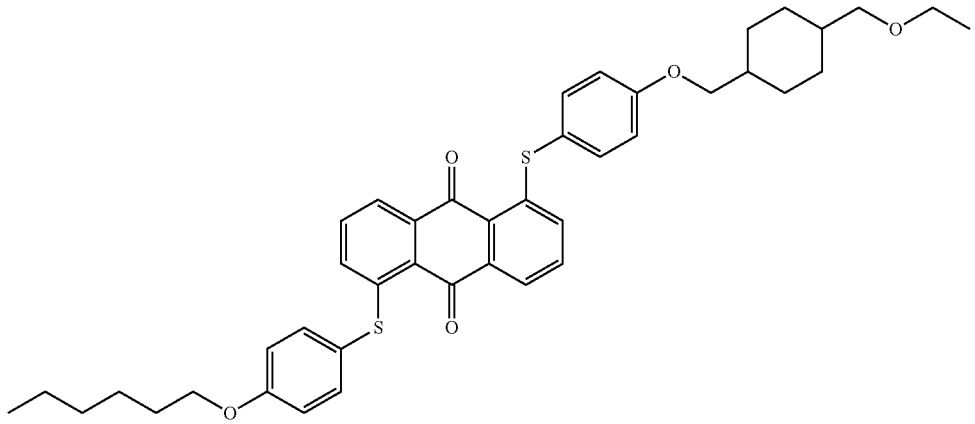

No.54

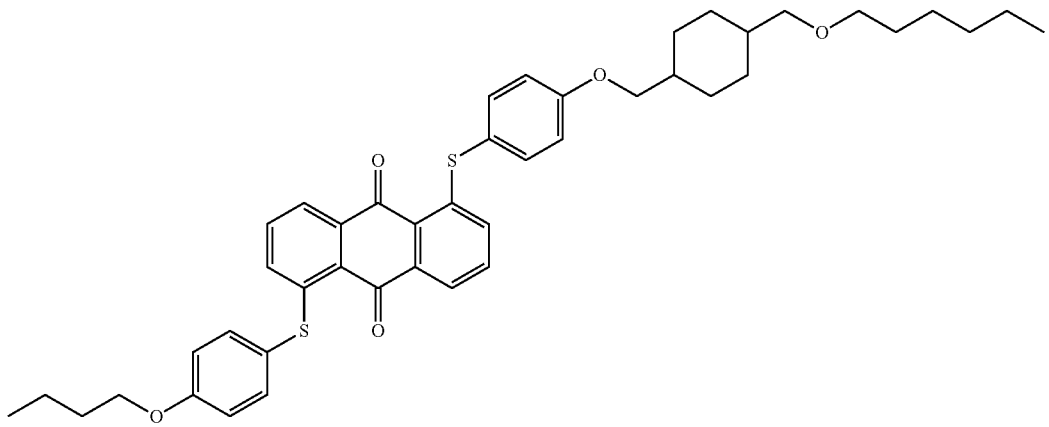

No.55

The compound represented by Formula (1) can be synthesized using a conventionally known method described in, for example, WO 87/02688.

The anthraquinone compound represented by Formula (1) of the present invention has a high order parameter (S value).

The order parameter (S value) in the present invention can be determined from the following formula described in "Liquid Crystal Device Handbook" (edited by 142th Committee of Japan Society for the Promotion of Science, published by Nikkan Kogyo Shimbun, Ltd., 1989) on the basis of spectroscopic measurement of the dichroic ratio of the anthraquinone compound (dichroic dye) represented by Formula (1).

$$S=(A_{//}-A_{\perp})/(2A_{\perp}+A_{//})$$

In the formula, "$A_{//}$" and "$A_{195}$" represent the absorbances of the dye for light polarized parallel and light polarized perpendicularly to the alignment direction of the liquid crystal, respectively. The calculated S value takes a value in a range of 0 to 1, and theoretically, the closer the value is to 1, the more the contrast in a GH (guest-host) light control element is improved.

The liquid crystal composition of the present invention (hereinafter, also simply referred to as "the composition of the present invention") contains the anthraquinone compound represented by Formula (1) and a liquid crystal material.

The content of the anthraquinone compound represented by Formula (1) in the liquid crystal composition is not particularly limited, and is preferably 0.5 to 10 parts by mass, and more preferably 0.5 to 5 parts by mass with respect to 100 parts by mass of the liquid crystal material. In the case of using a dichroic dye other than the compound represented by Formula (1) (described below) in combination, the total content of the anthraquinone compound represented by Formula (1) and the dichroic dye other than the compound represented by Formula (1) is preferably in the above range (0.5 to 10 parts by mass with respect to 100 parts by mass of the liquid crystal material).

The liquid crystal material contained in the liquid crystal composition of the present invention is not particularly limited as long as it is a material having liquid crystallinity (compound having liquid crystallinity) such as a nematic liquid crystal, a cholesteric liquid crystal, or a smectic liquid crystal, and among them, a nematic liquid crystal is preferable. Examples of the compound having liquid crystallinity include the liquid crystal compounds described in pages 154 to 192 and 715 to 722 of "Liquid Crystal Device Handbook" (edited by 142th Committee of Japan Society for the Promotion of Science, published by Nikkan Kogyo Shimbun, Ltd., 1989).

The liquid crystal composition of the present invention may contain a dichroic dye other than the anthraquinone compound represented by Formula (1), an optically active substance exhibiting a liquid crystal phase such as cholesteryl nonanoate, or an optically active substance not exhibiting a liquid crystal phase, and additives such as an ultraviolet absorber and an antioxidant, a photocurable compound, a photopolymerization initiator, and the like.

The photocurable compound that can be contained in the liquid crystal composition of the present invention is not particularly limited as long as it is a compound having a functional group that can be polymerized by the action of a photopolymerization initiator described below under irradiation with light. Examples of the photocurable compound include compounds having a (meth)acrylate group, compounds having a vinyl group, and compounds having an allyl group. Compounds having a (meth)acrylate group are preferable. In the present description, the term "(meth)acrylate" means "methacrylate and/or acrylate".

Examples of the (meth)acrylate compound contained in the liquid crystal composition of the present invention include mono(meth)acrylate compounds having one (meth)acrylate group in one molecule and di(meth)acrylate compounds having two (meth)actylate groups in one molecule.

As the mono(meth)acrylate compound, a mono(meth)acrylate having a C5-C13 linear, cyclic, or branched alkyl group is preferable. Specific examples of the mono(meth)acrylate compound include linear alkyl mono(meth)acrylates such as pentyl (meth)acrylate, hexyl (meth)acrylate, heptyl (meth)acrylate, octyl (meth)acrylate, nonyl (meth)acrylate, decyl (meth)acrylate, undecyl (meth)acrylate, dodecyl (meth)acrylate, and tridecyl (meth)acrylate, cyclic alkyl mono(meth)acrylates such as isobornyl (meth)acrylate, and branched alkyl mono(meth)acrylates such as 2-methylhexyl (meth)acrylate, 2-ethylhexyl (meth)acrylate, 2-propylhexyl (meth)acrylate, 2-methylheptyl (meth)acrylate, 2-ethytheptyl (meth)acrylate, and 2-propylheptyl (meth)acrylate.

Examples of the di(meth)acrylate compound include 1,4-butanediol di(meth)acrylate, 1,5-pentanediol di(meth)acrylate, 1,6-hexanediol di(meth)acrylate, 1,7-heptanediol di(meth)acrylate, 1,8-octanediol di(meth)acrylate, di(meth)acrylate, 1,10-decanediol di(meth)acrylate, 1,11-undecanediol di(meth)acrylate, 1,12-dodecanediol di(meth)acrylate, and 1,13-tridecanediol di(meth)acrylate, and trialkylene glycol di(meth)acrylates such as triethylene glycol di(meth)acrylate.

A mono(meth)acrylate compound and a di(meth)acrylate compound may be used in combination in the liquid crystal composition of the present invention. In the case of using a mono(meth)acrylate compound and a di(meth)acrylate compound in combination, the mass ratio of the mono(meth)acrylate compound to the di(meth)acrylate compound is preferably 10:90 to 96:4, and more preferably 50:50 to 95:5.

The photopolymerization initiator that can be contained in the composition of the present invention is not particularly limited as long as it is a compound capable of polymerizing a photocurable compound by irradiation with light. The photopolymerization initiator preferably does not cause deterioration of the dichroic dye such as the anthraquinone compound represented by Formula (1) by remaining in the cured product after irradiation with light.

Examples of the photopolymerization initiator preferably used include alkylphenone-based photopolymerization initiators such as Darocur 1173, Irgacure 651, and Irgacure 184, and phosphine oxide-based photopolymerization initiators such as Irgacure TPO.

In the composition of the present invention in the case of containing a photocurable compound and a photopolymerization initiator, the mass ratio of the total of the anthraquinone compound represented by Formula (1) and the liquid crystal material to the photocurable compound blended is preferably 90:10 to 50:50, more preferably 80:20 to 50:50, and still more preferably 65:35 to 50:50. If the ratio of the photocurable compound blended is set within the above range, the liquid crystal material and the photocurable compound can be prevented from separating from each other before curing by irradiation with light, and the cured product can be prevented from reduction in the light blocking property.

In the composition of the present invention in the case of using a dichroic dye other than the compound represented by Formula (1) in combination, the ratio of the total of all the dichroic dyes including the anthraquinone compound represented by Formula (1) and the liquid crystal material to the photocurable compound blended is preferably in the above range (a mass ratio of 90:10 to 50:50). The more preferable range and the still more preferable range are the same as those described above.

In the composition of the present invention in the case of containing a photocurable compound and a photopolymerization initiator, the content of the photopolymerization initiator is preferably 0.1 to 5 parts by mass with respect to 100 parts mass of the photocurable compound.

In the composition of the present invention, a dichroic dye other than the anthraquinone compound represented by Formula (1) can be used in combination.

Examples of the dichroic dye that can be used in combination include, but not limited to, an azo dye, an anthraquinone dye, a perylene dye, a quinophthalone dye, a merocyanine dye, an azomethine dye, a phthaloperylene dye, an indigo dye, an azulene dye, a dioxazine dye, a polythiophene dye, and the like. Specific examples of the dichroic dye include dichroic dyes described in "Dichroic dyes for Liquid Crystal Display" (A. V. Ivashchenko, CRC, 1994).

Among them, an azo dye, an anthraquinone dye, a perylene dye, or a quinophthalone dye is preferably used in combination, and an azo dye or an anthraquinone dye is more preferably used in combination.

In the case of using a dichroic dye other than the anthraquinone compound represented by Formula (1) in combination, the content of the anthraquinone compound represented by Formula (1) in all the dichroic dyes is not particularly limited as long as an effect of the present invention is not impaired. The amount of the anthraquinone compound is preferably 1 to 80 mass %, more preferably 5 to 70 mass %, and still more preferably 10 to 50 mass %.

In the composition of the present invention, a photostabilizer such as a benzotriazole-based, benzophenone-based, or hindered amine-based light stabilizer, an antioxidant such as a phosphite-based or hindered phenol-based antioxidant, a thermal polymerization inhibitor, a thiol compound, a photosensitizing agent, a photosensitizer, a chain transfer inhibitor, a polymerization inhibitor, an adhesiveness imparting agent, an antifoaming agent, a crosslinking agent, a surfactant, a thermosetting accelerator, a thermoplastic resin, a thermosetting resin, a thickener such as urethane diacrylate, and the like may be further used in combination.

Furthermore, in order to control the cell gap as a light control element, a spherical or cylindrical spacer of silica, glass, plastic, or ceramics may be added. The cell gap at this time can beet in a range of 2 to 100 μm.

The composition of the present invention is obtained by mixing and stirring the anthraquinone compound represented by Formula (1) and the liquid crystal material as essential components and, as necessary, a photocurable compound, a photopolymerization initiator, and an optional component to be added. Mixing and stirring may be performed with the simplest method in which all the components are put into a container and stirred manually, but a method is effective in which a device such as a magnetic stirrer is used for stirring. In order to prepare a uniform composition efficiently, it is preferable to prepare a uniform mixture of a photocurable compound, a photopolymerization initiator, and the liquid crystal material firstly; then add thereto the anthraquinone compound represented by Formula (1) and other optional component(s); and stir and mix them. At the time of stirring and mixing, heating may be performed as necessary. Stirring and mixing under a light source that emits an absorption wavelength of the photopolymerization initiator are preferably performed in as short a time as possible. After mixing the components, filtration may be further performed using a mesh, a membrane filter, or the like.

The composition of the present invention containing a photocurable compound and a photopolymerization initiator is irradiated with light to obtain a cured product of the liquid crystal composition in which the photocurable compound component is cured (polymerized). The term "cured product" in the present invention means a state in which the functional group of a photocurable compound is polymerized or copolymerized by irradiation with light, and does not necessarily mean a cured product in which the anthraquinone compound represented by Formula (1), the liquid crystal material, or the like contributes to the curing reaction.

The light source at the time of irradiation with light is not particularly limited as long as the light source can emit light having a wavelength absorbable by the photopolymerization initiator. Preferred examples of the light source include high-pressure mercury lamps capable of emitting ultraviolet rays, metal halide lamps, xenon lamps, and halogen lamps.

The light control element of the present invention includes a layer of the liquid crystal composition or the photocured product of the liquid crystal composition sandwiched between a pair of substrates disposed to face to each other in which at least one substrate in the pair of substrates is a transparent substrate having a transparent electrode. Here, examples of the substrate include substrates that are colorless and transparent, colored transparent, or opaque, such as inorganic transparent materials such as glass and quartz, metals, metal oxides, semiconductors, ceramics, plastic plates, and plastic films. The electrode is made by, for example, forming a thin film of a metal oxide, a metal, a semiconductor, an organic conductive material, or the like on the entire surface or a part of the substrate with a known coating method, a printing method, a vapor deposition method such as sputtering, or the like. In particular in order to obtain a light control element having a large area, it is desirable to use an electrode substrate in which an ITO (indium oxide, tin oxide) electrode is formed on a transparent polymer film such as PET using a vapor deposition method such as sputtering, a printing method, or the like from the viewpoint of productivity and processability. An aspect is more preferable in which both substrates in the pair of substrates are a transparent substrate having a transparent electrode. It is noted that wiring may be provided on the substrate to connect the electrodes together or connect the electrodes with an external device. For example, a segment driving electrode substrate, a matrix driving electrode substrate, an active matrix driving electrode substrate, or the like may be used. Furthermore, the surface of the electrode provided on the substrate may be entirely or partially covered with a protective film or an alignment film made of an organic compound such as a polyimide, a polyamide, a silicone compound, a cyan compound, an inorganic compound such as $SiO_2$, $TiO_2$, or $ZrO_2$, or a mixture thereof.

A flexible and lightweight light control element can be obtained by using a plastic film as the substrate. Therefore, the light control element can be sandwiched between a pair of films of flat or curved glass, hard plastic, or the like via an adhesive layer such as a polyvinyl butyral, vinyl acetate, a double-sided tape, or an adhesive and thus can be used. Alternatively, the light control element can be attached to a surface of a flat or curved film of glass, hard plastic, or the like with a double-sided tape, an adhesive, or the like and thus can be used. The light control element may be sandwiched between soft plastic films or attached to one side or both sides of a soft plastic film. A protective layer such as a hard coat, an ultraviolet cut layer, an infrared cut layer, or a half mirror also may be provided on the substrate surface opposite to the electrode surface of the light control element. A color filter may be layered, and/or a polarizer filter may be attached. The light control element may be layered with an electroluminescence display element, a light emitting diode display element, an electrochromic display element, or another liquid crystal display element.

A drive device for application of a voltage to the light control element of the present invention may be one capable of applying a DC voltage of 2 to 100 V or an AC voltage of 10 to 1000 Hz and capable of being made open or short-circuit the electrodes when no voltage is applied. The drive device may include a voltage application circuit for segment driving, a voltage application circuit for matrix driving, a voltage application circuit for active matrix, or the like.

The anthraquinone compound represented by Formula (1) of the present invention has a high order parameter, and the light control element using the liquid crystal composition containing the compound can realize high contrast display and is also excellent in light resistance and heat resistance after energization under long-term outdoor exposure. Therefore, the light control element is optimal for in-vehicle use or building material use.

EXAMPLES

Hereinafter, the present invention will be described in more detail with reference to Examples, however, the present invention is not limited thereto. The units "part" and "%" in the present text are on a mass basis unless otherwise specified. The maximum absorption wavelength in Examples is a value measured with a spectrophotometer "UV-3150" manufactured by SHIMADZU CORPORATION.

Example 1 (Synthesis of Anthraquinone Compound of Present Invention Represented by Formula (1))

(Step 1-1) Synthesis of Intermediate Compound Represented by Formula (2) Described Below To 120 parts of DMF, 10.0 parts of 1,5-dichloroanthraquinone, 7.3 parts of potassium carbonate, and 6.0 parts of 4-hydroxybenzenethiol were added, and the resulting mixture was stirred at 60° C. for 4 hours. The reaction liquid was cooled to 25° C., then 240 parts of methanol was added thereto, and the resulting mixture was stirred for 1 hour. The reaction product was collected by filtration and dried with a hot air dryer at 80° C. for 24 hours to obtain 6.3 parts of an intermediate compound represented by Formula (2) described below.

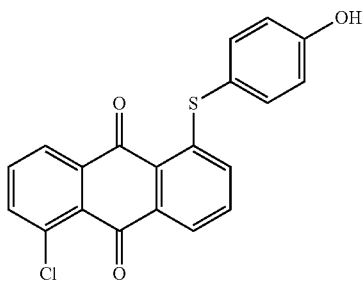

(2)

(Step 1-2) Synthesis of Intermediate Compound Represented by Formula (3) Described Below To 70 parts of DMF, 6.3 parts of the intermediate compound represented by Formula (2) obtained in the step (1-1), 3.6 parts of potassium carbonate, and 5.7 parts of 4-octylbenzenethiol were added thereto, and the resulting mixture was stirred at 60° C. for 2 hours. The reaction liquid was cooled to 25° C., then 140 parts of methanol was added, and the resulting mixture was stirred for 1 hour. The reaction product was collected by filtration, washed with toluene, and then dried with a hot air dryer at 80° C. for 24 hours to obtain 5.1 parts of an intermediate compound represented by Formula (3) described below.

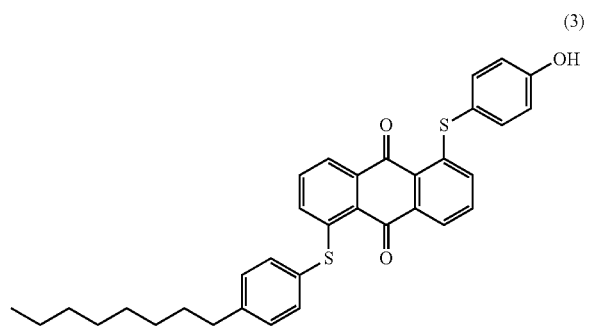 [SMILES: CCCCCCCCc1ccc(Sc2cccc3c2C(=O)c2cccc(Sc4ccc(O)cc4)c2C3=O)cc1]

(3)

Step (1-3) Synthesis of Compound Shown as Specific Example No. 7

To 50 parts of DMF, 5.1 parts of the intermediate compound represented by Formula (3) obtained in the step (1-2), 1.5 parts of potassium carbonate, and 2.2 parts of benzyl bromide were added, the resulting mixture was stirred at 100° C. for 2 hours, then the reaction liquid was cooled to 25° C. 200 parts of methanol was added thereto, and the resulting mixture was stirred for 1 hour. The reaction product was collected by filtration, washed with methanol, and then dried with a hot air dryer at 80° C. for 24 hours. The obtained crude product was dissolved in toluene and subjected to column purification using toluene as a developing solvent. The solvent was distilled off under reduced pressure from the solution after purification, and the resulting product was dried with a hot air dryer at 80° C. for 24 hours to obtain 4.0 parts of a compound shown as No. 7 of the above-described specific example in the form of an orange solid. The maximum absorption wavelength of this compound in methanol was 449 nm.

Example 2 (Synthesis of Anthraquinone Compound of Present Invention Represented by Formula (1))

Step (2-1) Synthesis of Compound Shown as Specific Example No. 10

Except that 5.7 parts of 4-octylbenzenethiol in the step 1-2 was changed to 4.3 parts of 4-n-butylbenzenethiol and that 2.2 parts of benzyl bromide in the step 1-3 was changed to 2.4 parts of 4-i-propylbenzyl Chloride, the same procedure as in Example 1 was carried out to obtain 3.3 parts of a compound shown as No. 10 of the above-described specific example in the form of an orange solid. The maximum absorption wavelength of this compound in methanol was 450 nm.

Example 3 (Synthesis of Anthraquinone Compound of Present Invention Represented by Formula (1)

(Step 3-1) Synthesis of Compound Shown as Specific Example No. 15

Except that 5.7 parts of 4-octylbenzenethiol in the step 1-2 was changed to 4.3 parts of 4-t-butylbenzenethiol and that 2.2 parts of benzyl bromide in the step 1-3 was changed to 2.4 parts of 4-t-butylbenzyl chloride, the same procedure as in Example 1 was carried out to obtain 3.5 parts of a compound shown as No. 15 of the above-described specific example in the form of an orange solid. The maximum absorption wavelength of this compound in methanol was 450 nm.

Example 4 (Synthesis of Anthraquinone Compound of Present Invention Represented by Formula (1))

(Step 4-1) Synthesis of Compound Shown as Specific Example No. 17

Except that 2.2 parts of benzyl bromide in the step 1-3 was changed to 2.4 parts of 4-t-butylbenzyl chloride, the same procedure as in Example 1 was carried out to obtain 3.0 parts of a compound shown as No. 17 of the above-described specific example in the form of an orange solid. The maximum absorption wavelength of this compound in methanol was 449 nm.

Example 5 (Synthesis of Anthraquinone Compound of Present Invention Represented by Formula (1))

(Step 5-1) Synthesis of Compound Shown as Specific Example No. 48

Except that 5.7 parts of 4-octylbenzenethiol in the step 1-2 was changed to 5.9 parts of 4-octyloxybenzenethiol and that 2.2 parts of benzyl bromide in the step 1-3 was changed to 2.4 parts of 4-t-butylbenzyl chloride, the same procedure as in Example 1 was carried out to obtain 3.9 parts of a compound shown as No. 48 of the above-described specific example in the form of an orange solid. The maximum absorption wavelength of this compound in methanol was 452 nm.

Synthesis Example 1 (Synthesis of Comparative Compound)

A compound shown as No. 2 in Table 2 of JP-A-63-72760 (i.e., a compound represented by Formula (X) described below) was obtained by a known synthesis method.

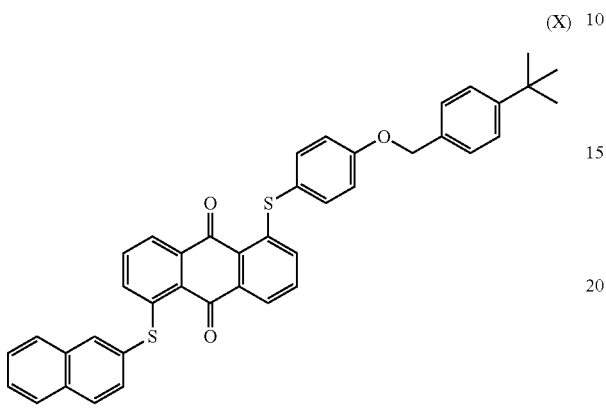

(X)

Synthesis Example 2 (Synthesis of Comparative Compound)

A compound shown as No. 1 in Table 2-1 of JP-A-62-101657 (i.e., a compound represented by Formula (Y) described below) was obtained by a known synthesis method.

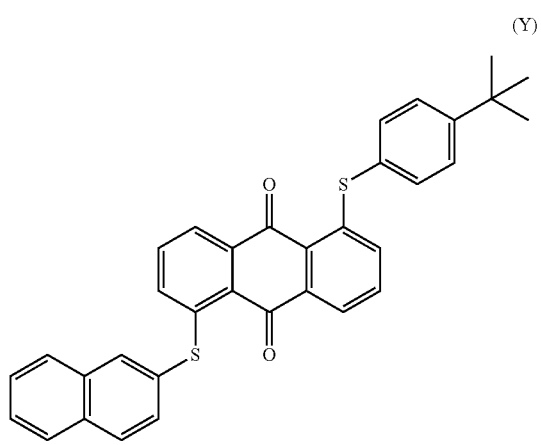 [SMILES: CC(C)(C)c1ccc(Sc2cccc3c2C(=O)c2cccc(Sc4ccc5ccccc5c4)c2C3=O)cc1]

(Y)

Synthesis Example 3 (Synthesis of Comparative Compound)

A compound shown in Example 11 in EP 59036 A1 (i.e., a compound represented by Formula (Z) described below) was obtained by a known synthesis method.

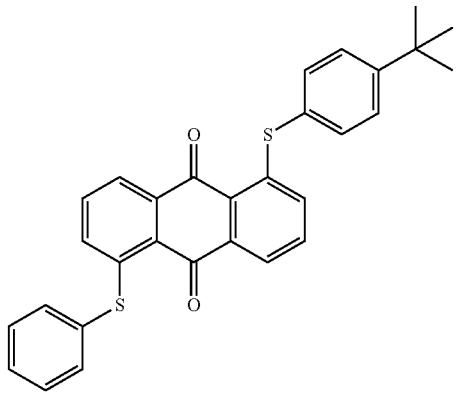

(Z)

Example 6 (Preparation of Liquid Crystal Composition of Present Invention)

A liquid crystal composition of the present invention was prepared by mixing 0.003 parts of the compound shown as specific example No. 7 obtained in Example 1, 0.306 parts of 1-cyano-4'-n-pentylbiphenyl, 0.15 parts of 1-cyano-4'-n-heptylbiphenyl, 0.096 parts of 1-cyano-4?-n-octyloxybiphenyl, and 0.048 parts of 1-cyano-4"-n-pentylterphenyl at room temperature.

Examples 7 to 10 and Comparative Examples 1 to 3 (Preparation of Liquid Crystal Compositions of Present Invention and Comparative Liquid Crystal Compositions)

Liquid crystal compositions of the present invention and comparative liquid crystal compositions were obtained as in Example 6 except that the compound shown as specific example No. 7 obtained in Example 1 was changed to the compound shown as specific example No. 10 obtained in Example 2, the compound shown as specific example No. 15 obtained in Example 3, the compound shown as specific example No. 17 obtained in Example 4, the compound shown as specific example No. 48 obtained in Example 5, the compound represented by Formula (X) obtained in Synthesis Example 1, the compound represented by Formula (Y) obtained in Synthesis Example 2, and the compound represented by Formula (Z) obtained in Synthesis Example 3, respectively.

Example 11 (Production of Light Control Element of Present Invention)

The liquid crystal composition obtained in Example 6 was sealed in an element that included upper and lower two glass substrates, with an inter-substrate gap of 15 μm, having a transparent electrode and subjected to a homogeneous alignment treatment by rubbing a polyamide-based resin on a surface to be in contact with the liquid crystal. In the element thus obtained, the liquid crystal was in a homogeneous alignment state when no voltage was applied, and the dye molecules (i.e., the anthraquinone compound obtained in Example 1) were also in a similar alignment state depending on the liquid crystal.

Examples 12 to 15 and Comparative Examples 4 to 6 (Production of Light Control Elements of Present Invention and Comparative Light Control Elements)

Light control elements of the present invention and comparative light control elements were produced as in Example 11 except that the liquid crystal composition obtained in Example 6 was changed to each of the liquid crystal compositions of Examples 7 to 10 and Comparative Examples 1 to 3.

(Calculation of Order Parameter of Light Control Element)

For the light control elements obtained in Examples 11 to 15 and Comparative Examples 4 to 6, the maximum absorption wavelength and the order parameter were measured. Linearly polarized light parallel to the alignment direction and linearly polarized light perpendicular to the alignment direction were incident on each of the obtained light control elements. From each spectrum at this time, the absorbance for linearly polarized light parallel to the alignment direction of the colored cell ($A_{//}$) and the absorbance for polarized light perpendicular to the alignment direction ($A_\perp$) were measured, and the order parameter (S value) at the maximum absorption wavelength at which the polarization degree ρ was the largest was determined from the following formula. Table 1 shows the results.

$$S=(A_{//}-A_\perp)/(2A_\perp+A_{//})$$

TABLE 1

Calculation results of order parameter (S value)

| Light control element | Maximum absorption wavelength (nm) | S value |
|---|---|---|
| Example 11 No. 7 Compound | 464 | 0.81 |
| Example 12 No. 10 Compound | 465 | 0.81 |
| Example 13 No. 15 Compound | 465 | 0.80 |
| Example 14 No. 17 Compound | 465 | 0.81 |
| Example 15 No. 48 Compound | 466 | 0.82 |
| Comparative Example 4 Compound of Formula (X) | 464 | 0.79 |
| Comparative Example 5 Compound of Formula (Y) | 464 | 0.77 |
| Comparative Example 6 Compound of Formula (Z) | 465 | 0.73 |

As shown in Table 1, it is apparent that the light control elements of Examples 11 to 15 each had a higher order parameter and are more excellent as a light control element than the light control elements of Comparative Examples 4 to 6.

Example 16 (Preparation of Liquid Crystal Composition of Present Invention)

At room temperature, 0.01 parts of the compound shown as specific example No. 10 obtained in Example 2, 0.380 parts of isobornyl acrylate (monoacrylate manufactured by OSAKA ORGANIC CHEMICAL INDUSTRY LTD.), 0.020 parts of triethylene glycol dimethacrylate (manufactured by SHIN-NAKAMURA CHEMICAL Co., Ltd.), 0.306 parts of 1-cyano-4'-n-pentylbiphenyl, 0.15 parts of 1-cyano-4'-n-heptylbiphenyl, 0.096 parts of 1-cyano-4'-n-octyloxybiphenyl, 0.048 parts of 1-cyano-4"-n-pentylterphenyl, 0.004 parts of Irgacure TPO (manufactured by BASF SE), 0.004 parts of Irgacure 184 (manufactured by BASF SE), and 0.010 parts of a spacer agent having a size of 20 μm ("Micropearl (registered trademark) SP 220" manufactured by SEKISUI CHEMICAL CO., LTD.) were mixed, and stirred at 50° C. for 2 hours. Then, the resulting mixed liquid was cooled to room temperature and passed through a 1 μm membrane filter to prepare a liquid crystal composition of the present invention.

Examples 17 and 18 and Comparative Example 7 (Preparation of Liquid Crystal Compositions of Present Invention and Comparative Liquid Crystal Composition)

Liquid crystal compositions of the present invention and a comparative liquid crystal composition were obtained as in Example 16 except that the compound shown as specific example No. 10 obtained in Example 2 was changed to each of the compound shown as specific example No. 15 obtained in Example 3, the compound shown as specific example No, 17 obtained in Example 4, and the compound represented by Formula (X) obtained in Synthesis Example 1.

Examples 19 to 21 and Comparative Example 8 (Production of Light Control Elements of Present Invention and Comparative Light Control Element)

Each of the liquid crystal compositions obtained in Examples 16 to 18 and Comparative Example 7 was applied using an applicator onto an ITO film provided on a 5 cm square PET film to form a liquid crystal composition layer. Next, this film and a 5 cm square PET film provided with an ITO film equivalent to the above-described ITO film were superimposed so that the liquid crystal composition layer on the ITO film and the other ITO film faced each other. Thereafter, while the laminate sample including the two films and the liquid crystal composition layer obtained as described above was maintained at 23° C. with a thermoplate, the sample was set at a position where the intensity of light of 365 nm from an LED lamp was 9 mW/cm², and irradiated with light for 1 minute to photocure the photocurable compound, and thus light control elements of the present invention and a comparative light control element were obtained.

(Calculation of Transmittance Difference of Light Control Element)

For each of the light control elements obtained in Examples 19 to 21 and Comparative Example 8, the maximum absorption wavelength was measured with the above-described method, and the transmittance difference (i.e., transmittance change) was calculated from the measurement results of the transmittance (%) at the maximum absorption wavelength at the time of applying an AC voltage of 100 V (50 Hz sine wave) and at the time of applying no voltage.

TABLE 2

Calculation results of transmittance difference

| Light control element | Maximum absorption wavelength (nm) | Transmittance difference |
|---|---|---|
| Example 19 No. 10 Compound | 448 | 42 |

TABLE 2-continued

Calculation results of transmittance difference

| Light control element | Maximum absorption wavelength (nm) | Transmittance difference |
|---|---|---|
| Example 20 No. 15 Compound | 449 | 41 |
| Example 21 No. 17 Compound | 448 | 43 |
| Comparative Example 8 Compound of Formula (X) | 455 | 36 |

As shown in Table 2, it is apparent that the light control elements of Examples 19 to 21 each had a larger transmittance difference between the time of applying a voltage and the time of applying no voltage than the light control element of Comparative Example 8.

Example 22 (Production of Black Light Control Element)

A black light control element was produced in the same manner as in Examples 19 to 21 using a liquid crystal composition of the present invention prepared in the same manner as in Example 16 except that 0.012 parts of LCD 121 (anthraquinone-based compound manufactured by Nippon Kayaku Co., Ltd.) and 0.009 parts of LCD 212 (anthraquinone-based compound manufactured by Nippon Kayaku Co., Ltd.) were added. The obtained black light control element had an average transmittance difference of 32% at 400 to 700 nm, and thus exhibited high contrast.

The black light control element obtained in Example 22 had no change in transmittance even after a lapse of 500 hours in a xenon light resistance test, and was also excellent in light resistance under long-time exposure to light. Furthermore, the transmittance did not change even in the case of applying an AC voltage of 100 V (50 Hz sine wave) under the condition of 110° C., and thus the heat resistance after energization was also excellent. These results reveal that the black light control element of Example 22 is a black liquid crystal light control element having high contrast, excellent light resistance, and excellent heat resistance after energization.

INDUSTRIAL APPLICABILITY

A light control element excellent in contrast, light resistance, and heat resistance after energization can be obtained by using a liquid crystal composition containing the anthraquinone compound of the present invention. The light control element having these excellent properties is suitable for in-vehicle use or building material use.

The invention claimed is:

1. An anthraquinone compound represented by Formula (1) described below:

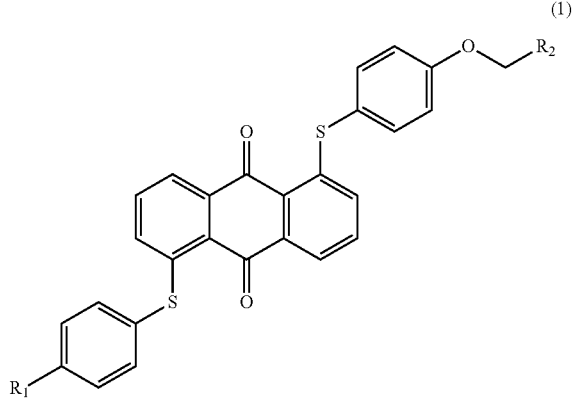

wherein $R_1$ represents a hydrogen atom, a C1-C12 linear alkyl group or a C3-C12 branched alkyl group, or a C1-C12 linear alkoxy group or a C3-C12 branched alkoxy group, and $R_2$ represents a substituent represented by Formula (a) described below:

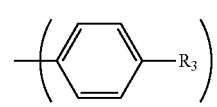

wherein $R_3$ represents a hydrogen atom, a C1-C8 linear alkyl group or a C3-C8 branched alkyl group, a C1-C8 linear alkoxy group or a C3-C8 branched alkoxy group, or a substituent represented by —$CH_2OR_4$ wherein $R_4$ represents a C1-C8 linear alkyl group or a C3-C8 branched alkyl group or $R_2$ represents a substituent represented by Formula (b) described below:

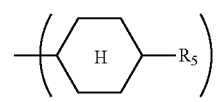

wherein $R_5$ represents a hydrogen atom, a C1-C8 linear alkyl group or a C3-C8 branched alkyl group, or a substituent represented by —$CH_2OR_6$ wherein $R_6$ represents a C1-C8 linear alkyl group or a C3-C8 branched alkyl group.

2. The anthraquinone compound according to claim 1, wherein $R_2$ in Formula (1) represents a substituent represented by Formula (a), and $R_3$ in Formula (a) represents a hydrogen atom, a C1-C8 linear alkyl group or a C3-C8 branched alkyl group, or a C1-C8 linear alkoxy group or a C3-C8 branched alkoxy group.

3. The anthraquinone compound according to claim 2, wherein $R_3$ in Formula (a) represents a hydrogen atom or a C1-C8 linear alkyl group or a C3-C8 branched alkyl group.

4. The anthraquinone compound according to claim 1, wherein $R_2$ in Formula (1) represents a substituent represented by Formula (b), and $R_5$ in Formula (b) represents a hydrogen atom or a C1-C8 linear alkyl group or a C3-C8 branched alkyl group.

5. The anthraquinone compound according to claim 1, wherein $R_1$ in Formula (1) represents a C1-C8 linear alkoxy group or a C3-C8 branched alkoxy group.

6. The anthraquinone compound according to claim 5, wherein $R_1$ in Formula (1) represents a C4-C8 linear alkoxy group.

7. The anthraquinone compound according to claim 1, wherein $R_1$ in Formula (1) represents a hydrogen atom or a C1-C8 linear alkyl group or a C3-C8 branched alkyl group.

8. The anthraquinone compound according to claim 7, wherein $R_1$ in Formula (1) represents a C4-C8 linear alkyl group.

9. A liquid crystal composition comprising the anthraquinone compound according to claim 1 and a liquid crystal material.

10. The liquid crystal composition according to claim 9, further comprising a photocurable compound and a photopolymerization initiator.

11. The liquid crystal composition according to claim 9, further comprising at least one dye compound other than the anthraquinone compound represented by Formula (1) described below, wherein said dye compound other than the anthraquinone compound represented by Formula (1) comprises at least one dye selected from the group consisting of an azo dye, an anthraquinone dye, a perylene dye, a quinophthalone dye, a merocyanine dye, an azomethine dye, a phthaloperylene dye, an indigo dye, an azulene dye, a dioxazine dye, and a polythiophene dye:

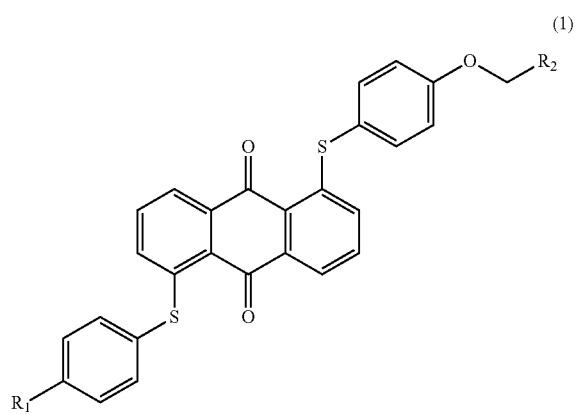

(1)

wherein $R_1$ represents a hydrogen atom, a C1-C12 linear alkyl group or a C3-C12 branched alkyl group, or a C1-C12 linear alkoxy group or a C3-C12 branched alkoxy group, and $R_2$ represents a substituent represented by Formula (a) described below:

(a)

wherein $R_3$ represents a hydrogen atom, a C1-C8 linear alkyl group or a C3-C8 branched alkyl group, a C1-C8 linear alkoxy group or a C3-C8 branched alkoxy group, or a substituent represented by —$CH_2OR_4$ wherein $R_4$ represents a C1-C8 linear alkyl group or a C3-C8 branched alkyl group or $R_2$ represents a substituent represented by Formula (b) described below:

(b)

wherein $R_5$ represents a hydrogen atom, a C1-C8 linear alkyl group or a C3-C8 branched alkyl group, or a substituent represented by —$CH_2OR_6$ wherein $R_6$ represents a C1-C8 linear alkyl group or a C3-C8 branched alkyl group.

12. A photocured product of the liquid crystal composition according to claim 10.

13. A light control element comprising: a pair of substrates disposed to face to each other; and the liquid crystal composition according to claim 9 sandwiched between the pair of substrates, wherein at least one substrate in the pair of substrates is a transparent substrate having thereon a transparent electrode.

14. The light control element according to claim 13, wherein both substrates in the pair of substrates are a transparent substrate having thereon a transparent electrode.

15. The liquid crystal composition according to claim 10, further comprising a dye compound other than the anthraquinone compound represented by Formula (1) described below, wherein said dye compound other than the anthraquinone compound represented by Formula (1) comprises at least one dye selected from the group consisting of an azo dye, an anthraquinone dye, a perylene dye, a quinophthalone dye, a merocyanine dye, an azomethine dye, a phthaloperylene dye, an indigo dye, an azulene dye, a dioxazine dye, and a polythiophene dye:

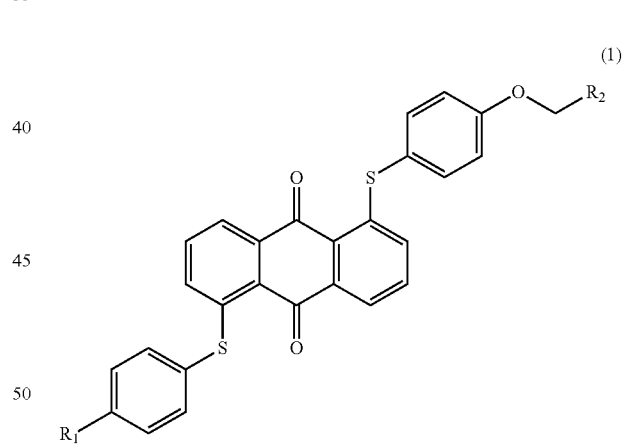

(1)

wherein $R_1$ represents a hydrogen atom, a C1-C12 linear alkyl group or a C3-C12 branched alkyl group, or a C1-C12 linear alkoxy group, or a C3-C12 branched alkoxy group and $R_2$ represents a substituent represented by Formula (a) described below:

(a)

wherein $R_3$ represents a hydrogen atom, a C1-C8 linear alkyl group or a C3-C8 branched alkyl group, a C1-C8 linear alkoxy group or a C3-C8 branched alkoxy group, or a substituent represented by —$CH_2OR_4$ wherein $R_4$ represents a C1-C8 linear alkyl group or a C3-C8 branched alkyl group or $R_2$ represents a substituent represented by Formula (b) described below:

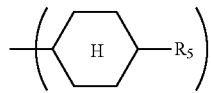
(b)

wherein $R_5$ represents a hydrogen atom, a C1-C8 linear alkyl group or a C3-C8 branched alkyl group, or a substituent represented by —$CH_2OR_6$ wherein $R_6$ represents a C1-C8 linear alkyl group or a C3-C8 branched alkyl group.

16. A photocured product of the liquid crystal composition according to claim 11.

17. A photocured product of the liquid crystal composition according to claim 15.

18. A light control element comprising: a pair of substrates disposed to face to each other; and the photocured product according to claim 12 sandwiched between the pair of substrates, wherein at least one substrate in the pair of substrates is a transparent substrate having thereon a transparent electrode.

19. A light control element comprising: a pair of substrates disposed to face to each other; and the photocured product according to claim 16 sandwiched between the pair of substrates, wherein at least one substrate in the pair of substrates is a transparent substrate having thereon a transparent electrode.

20. A light control element comprising: a pair of substrates disposed to face to each other; and the photocured product according to claim 17 sandwiched between the pair of substrates, wherein at least one substrate in the pair of substrates is a transparent substrate having thereon a transparent electrode.

* * * * *